(12) United States Patent
Kim et al.

(10) Patent No.: US 10,689,668 B2
(45) Date of Patent: Jun. 23, 2020

(54) STRAIN PRODUCING ALLOSE FROM FRUCTOSE AND METHOD FOR PRODUCING ALLOSE USING SAME

(71) Applicant: SAMYANG CORPORATION, Seoul (KR)

(72) Inventors: Min Jeong Kim, Suwon-si (KR); Eun Jin Han, Seoul (KR); Jeong Min Kim, Daejeon (KR); Hye Jung Kim, Daejeon (KR); Chong Jin Park, Daejeon (KR); Kang Pyo Lee, Seoul (KR); Eun-Soo Choi, Daejeon (KR); Jeongyoon Choi, Seongnam-si (KR)

(73) Assignee: SAMYANG CORPORATION, Seoul (KR)

( * ) Notice: Subject to any disclaimer, the term of this patent is extended or adjusted under 35 U.S.C. 154(b) by 94 days.

(21) Appl. No.: 16/060,480

(22) PCT Filed: Dec. 1, 2016

(86) PCT No.: PCT/KR2016/014059
§ 371 (c)(1),
(2) Date: Jun. 8, 2018

(87) PCT Pub. No.: WO2017/111339
PCT Pub. Date: Jun. 29, 2017

(65) Prior Publication Data
US 2019/0017070 A1    Jan. 17, 2019

(30) Foreign Application Priority Data
Dec. 21, 2015 (KR) .................. 10-2015-0183246

(51) Int. Cl.
*A61K 38/51* (2006.01)
*C12N 15/861* (2006.01)
*C12P 19/02* (2006.01)
*C12N 9/90* (2006.01)
*C12N 9/96* (2006.01)
*C12N 15/63* (2006.01)
*C12N 15/52* (2006.01)

(52) U.S. Cl.
CPC ............. *C12N 15/861* (2013.01); *C12N 9/90* (2013.01); *C12N 9/96* (2013.01); *C12N 15/52* (2013.01); *C12N 15/63* (2013.01); *C12P 19/02* (2013.01); *C12Y 501/03* (2013.01)

(58) Field of Classification Search
CPC .................... C12P 19/24; C12N 9/90

USPC ..................................................... 424/94.5
See application file for complete search history.

(56) References Cited

U.S. PATENT DOCUMENTS

| | | | |
|---|---|---|---|
| 7,381,544 B2 | 6/2008 | Gilbert et al. | |
| 8,735,106 B2 * | 5/2014 | Hong ................. | C12N 9/90 435/105 |
| 2009/0068710 A1 | 3/2009 | Izumori et al. | |
| 2015/0230509 A1 | 8/2015 | Fujihara et al. | |

FOREIGN PATENT DOCUMENTS

| | | |
|---|---|---|
| EP | 2918677 | 9/2015 |
| JP | 2003-523715 | 8/2003 |
| JP | 2012-070708 | 4/2012 |
| KR | 10-2012-0004492 | 1/2012 |
| KR | 10-1318422 | 10/2013 |
| KR | 10-2014-0021974 | 2/2014 |
| KR | 10-2015-0076051 | 7/2015 |
| KR | 10-2015-0076257 | 7/2015 |
| WO | 2012-006061 | 1/2012 |
| WO | 2015-032761 | 3/2015 |

OTHER PUBLICATIONS

S. H. Bhuiyan et al., "D-Allose Production from D-Psicose Using Immobilized L-Rhamnose Isomerase", Journal of Fermentation and Bioengineering, vol. 85, No. 5, pp. 539-541, 1998.
Francois Baneyx, "Recombinant protein expression in *Escherichia coli*", Current Opinion Biotechnology 1999, vol. 10, pp. 411-421, 1999, Expression vectors and delivery systems.
Anonymous: "ribose 5-phosphate isomerase B [Persephonella marina]", NCBI Reference Sequence: WP_015898864.1, Retrieved from the Internet: URL: https://www.ncbi.nlm.nih.gov/protein/WP_015898864.1 [retrieved on Jan. 13, 2020].
Deok-Kun Oh et al., "Production of medical rare sugar, psicose and allose by bioconversion", KOSEF, Nov. 30, 2007.
Buetusiwa Thomas Menavuvu et al., "Efficient Biosynthesis of D-Allose from D-Psicose by Cross-linked Recombinant L-Rhamnose Isomerase: Separation of Product by Ethanol Crystallization", Journal of Bioscience and Bioengineering, vol. 101, No. 4, p. 340-345, 2006.
EPO, the extended European search report of EP 16879206.7 dated May 9, 2019.

* cited by examiner

*Primary Examiner* — Tekchand Saidha
(74) *Attorney, Agent, or Firm* — Lex IP Meister, PC

(57) ABSTRACT

The present invention relates to a recombinant strain for producing an allose from a fructose, a composition for producing an allose which produces an allose from a fructose-containing raw material comprising the strain, and a method for preparing an allose using the same.

4 Claims, 21 Drawing Sheets

Specification includes a Sequence Listing.

[Fig. 1]
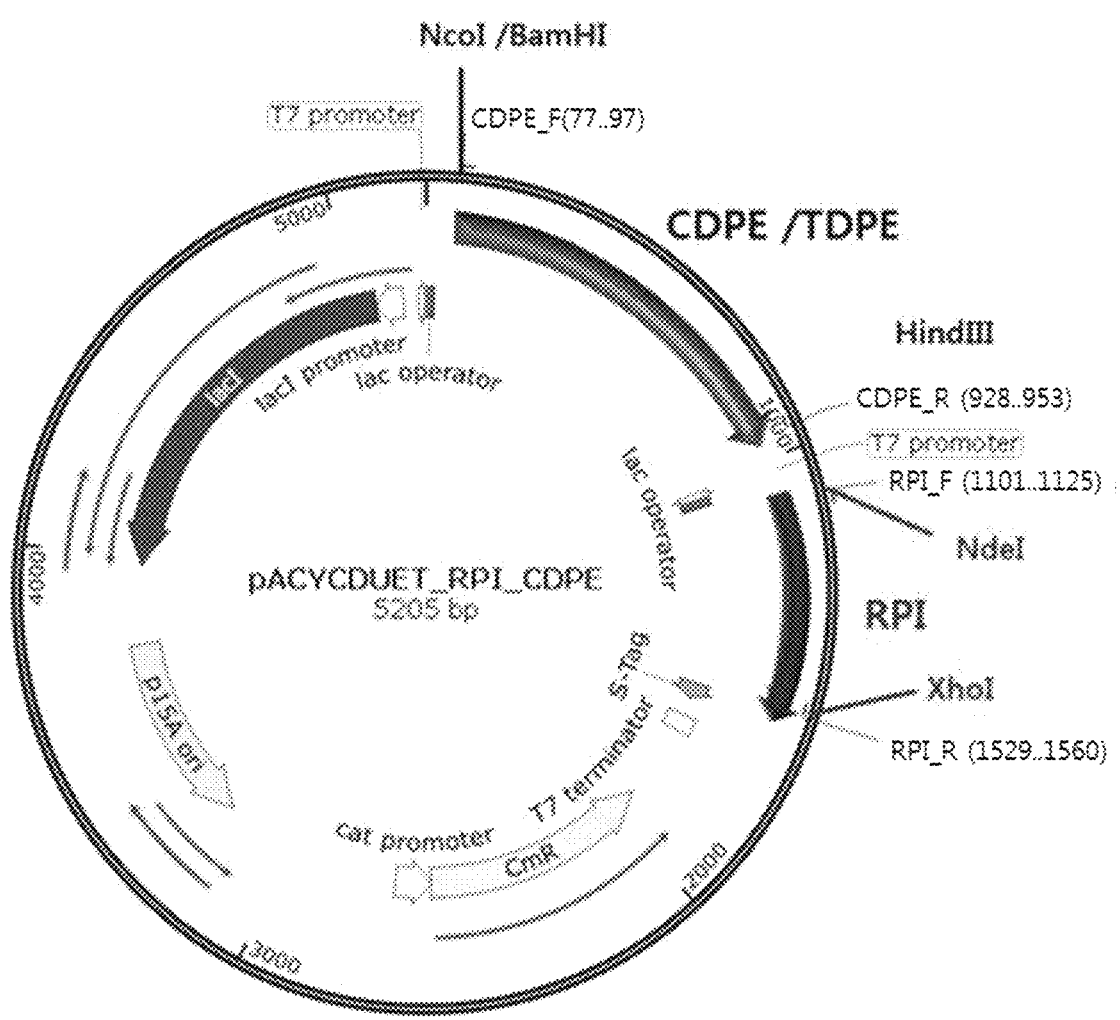

[Fig. 2]
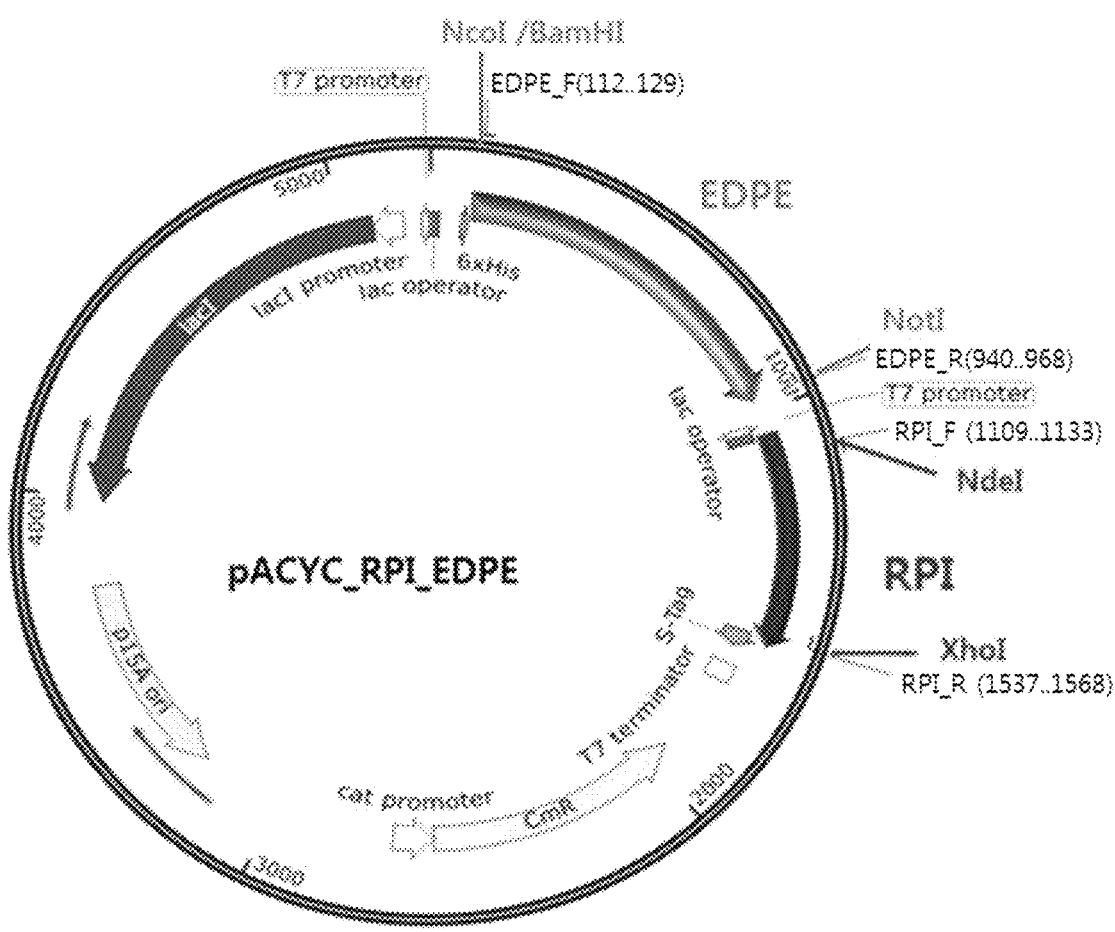

[Fig. 3]
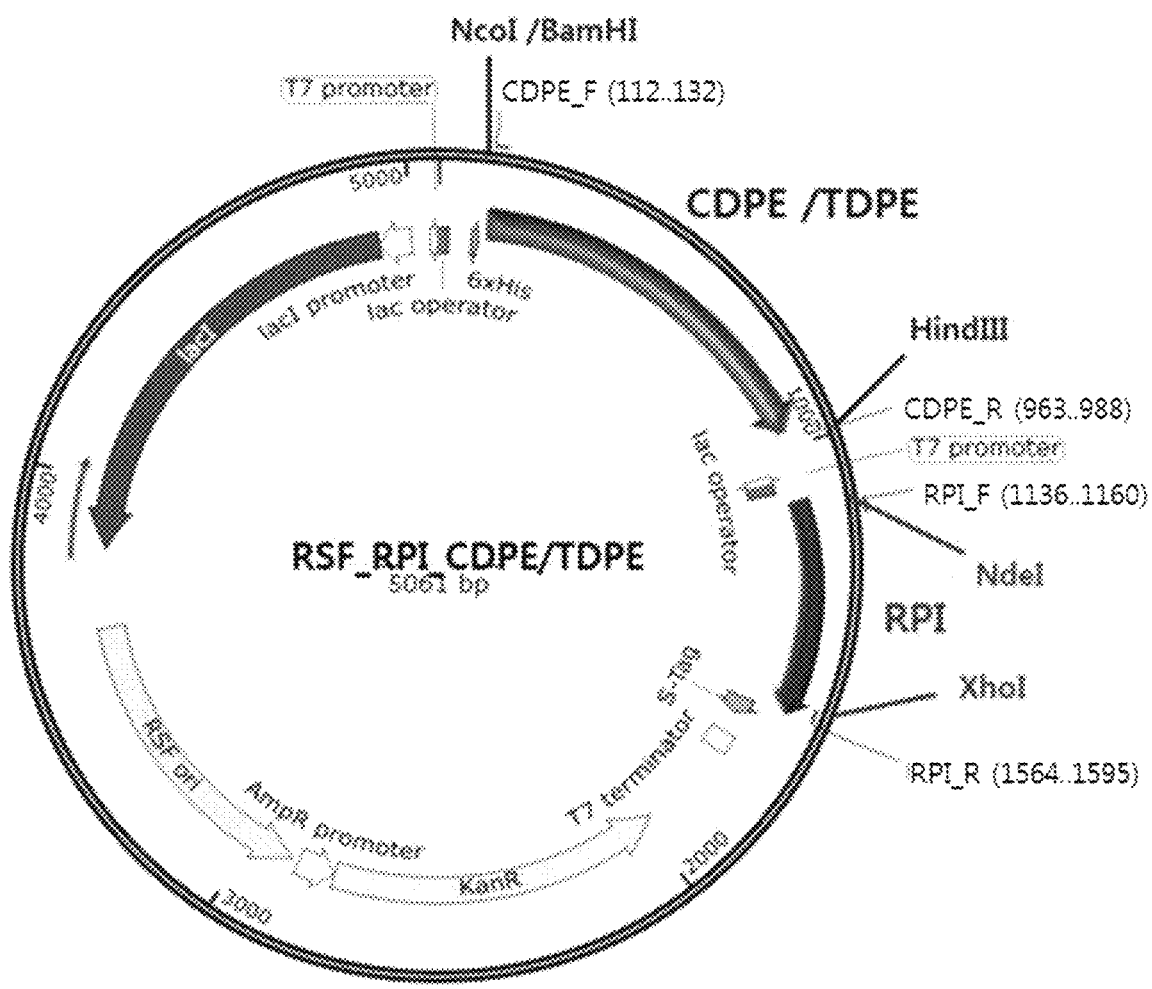

[Fig. 4]
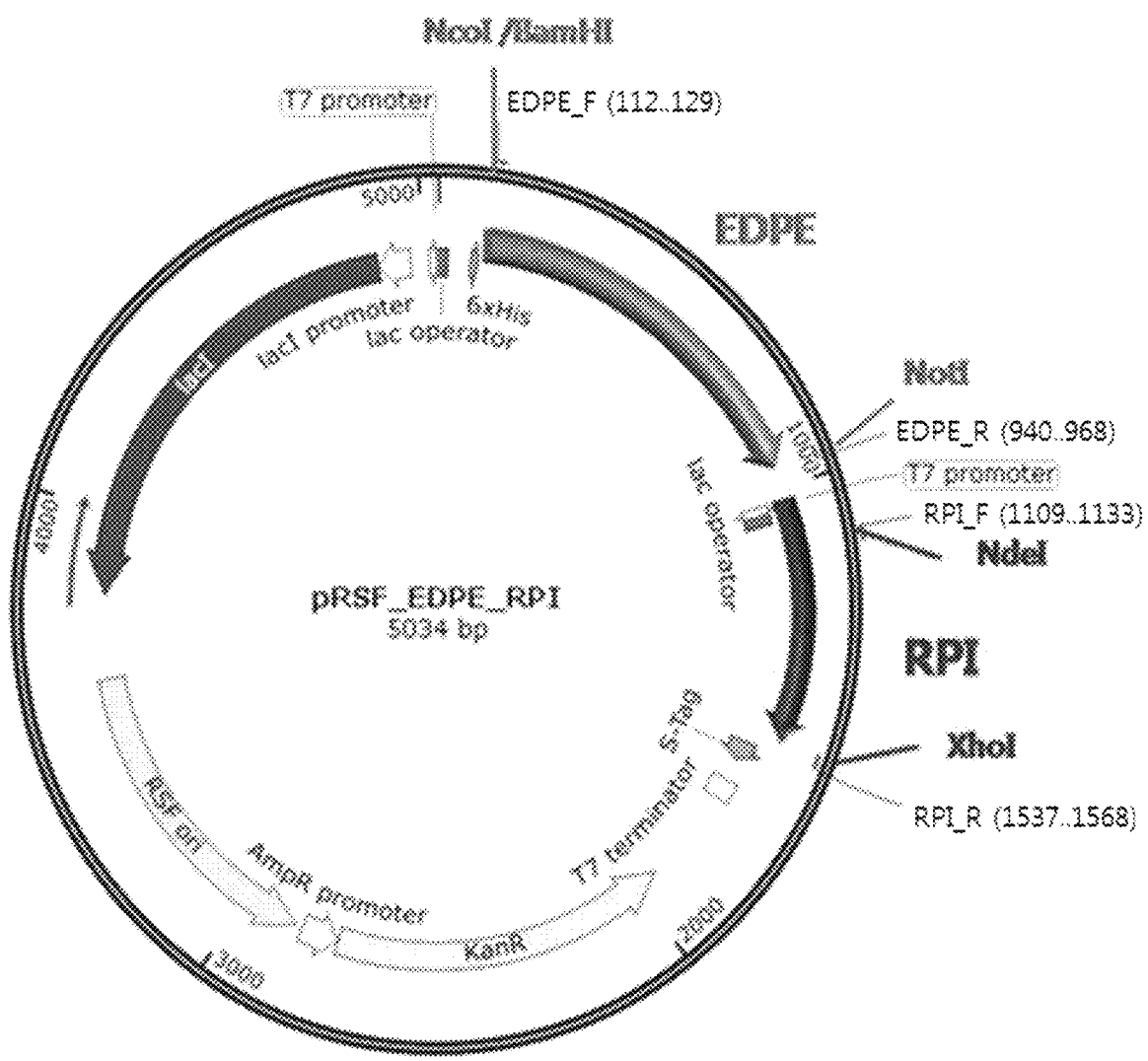

[Fig. 5]
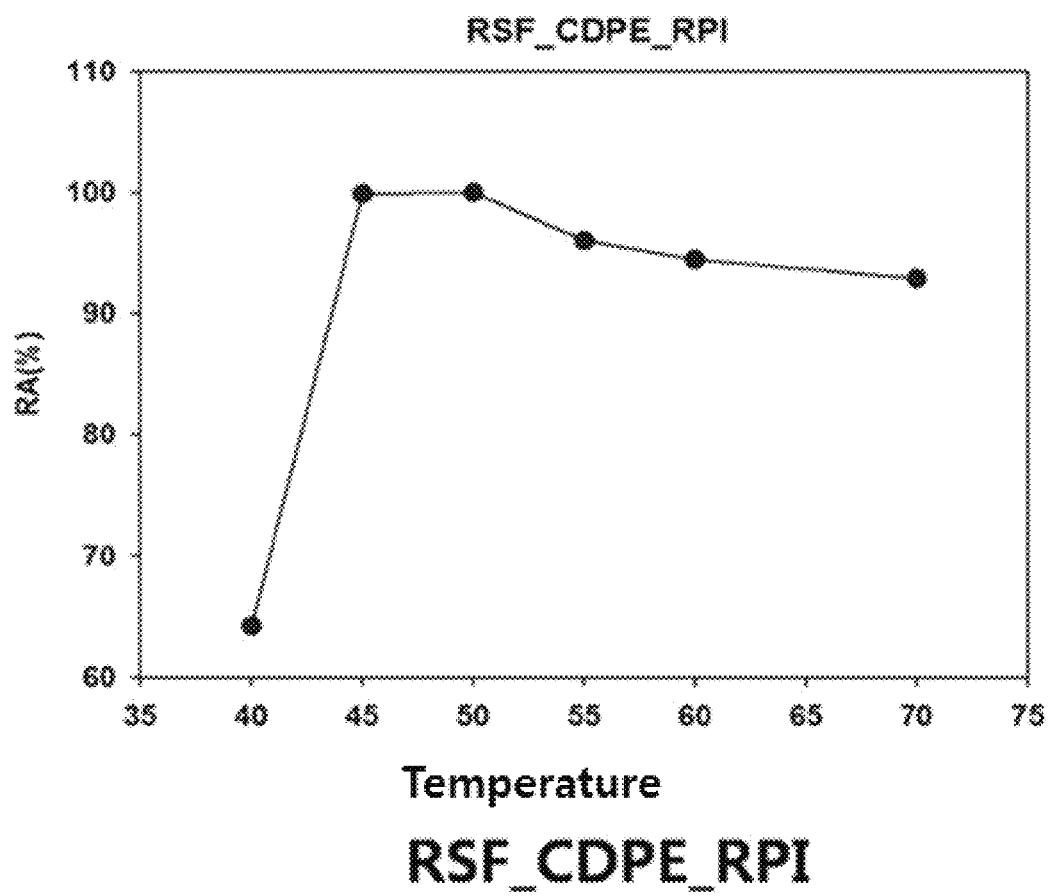
RSF_CDPE_RPI

[Fig. 6]
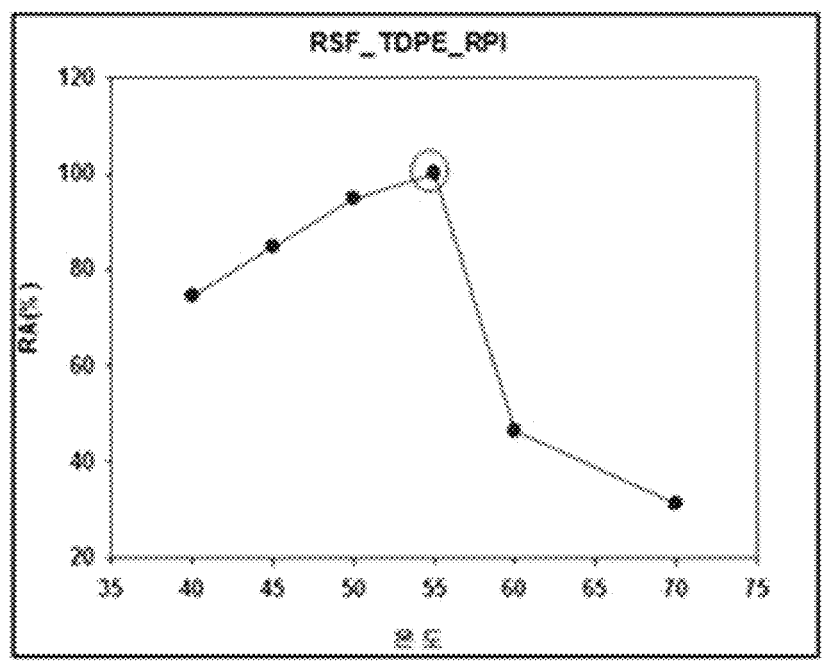
RSF_TDPE_RPI

[Fig. 7]
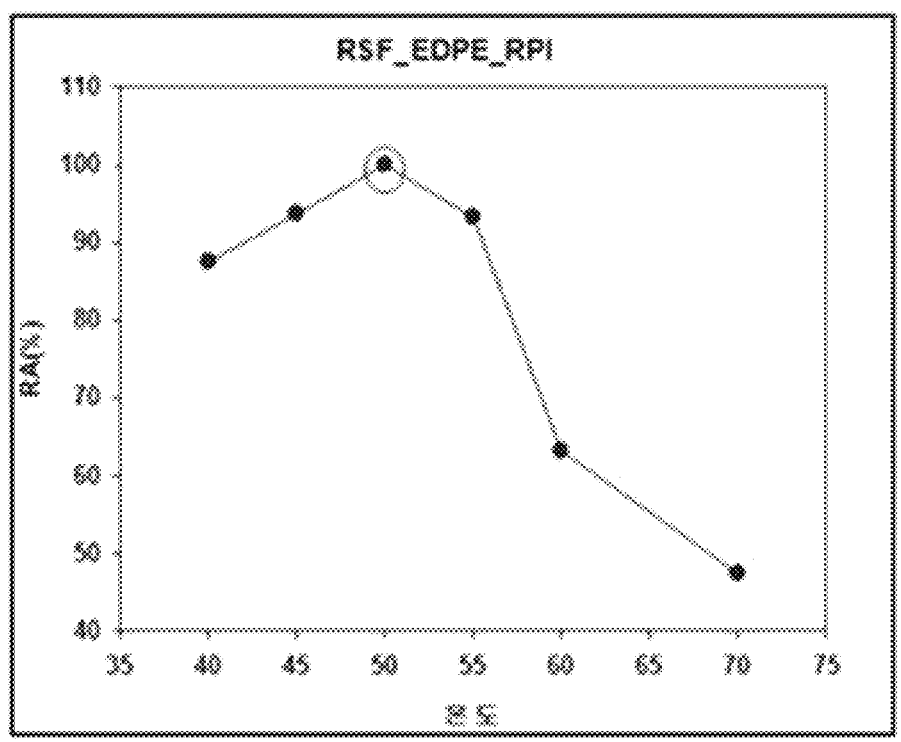
RSF_EDPE_RPI

[Fig. 8]
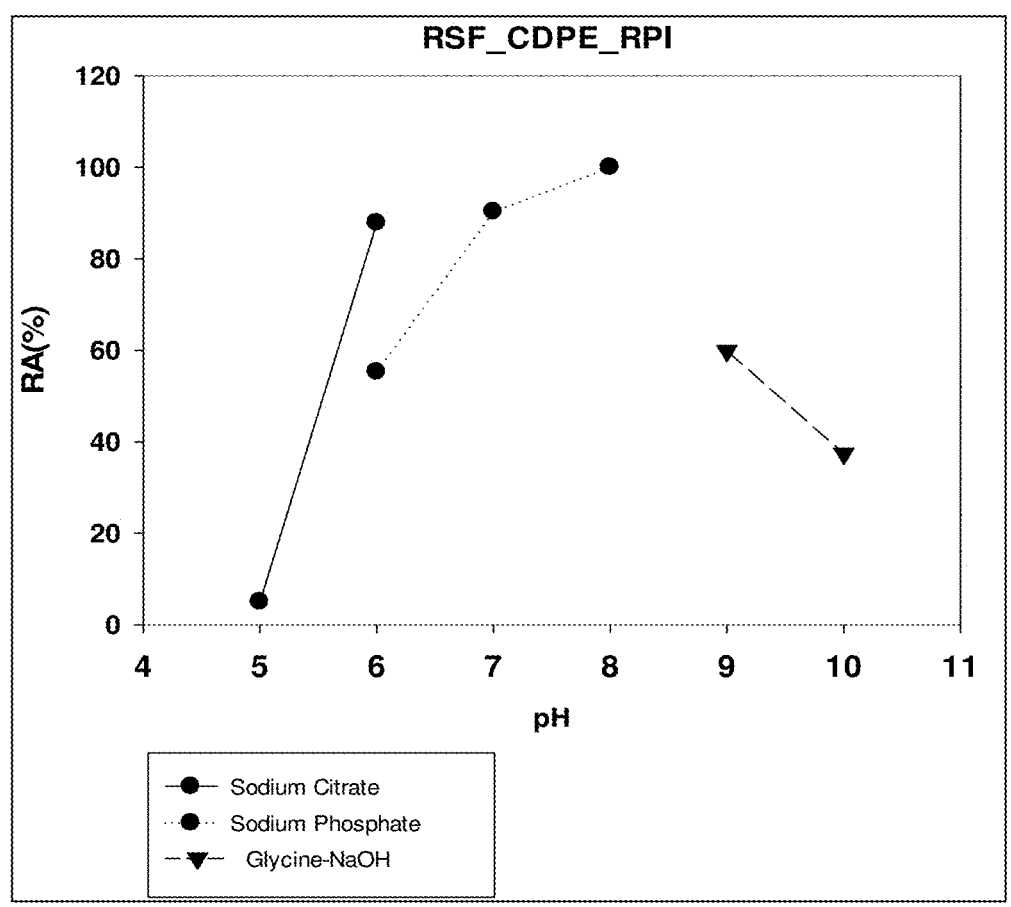

[Fig. 9]
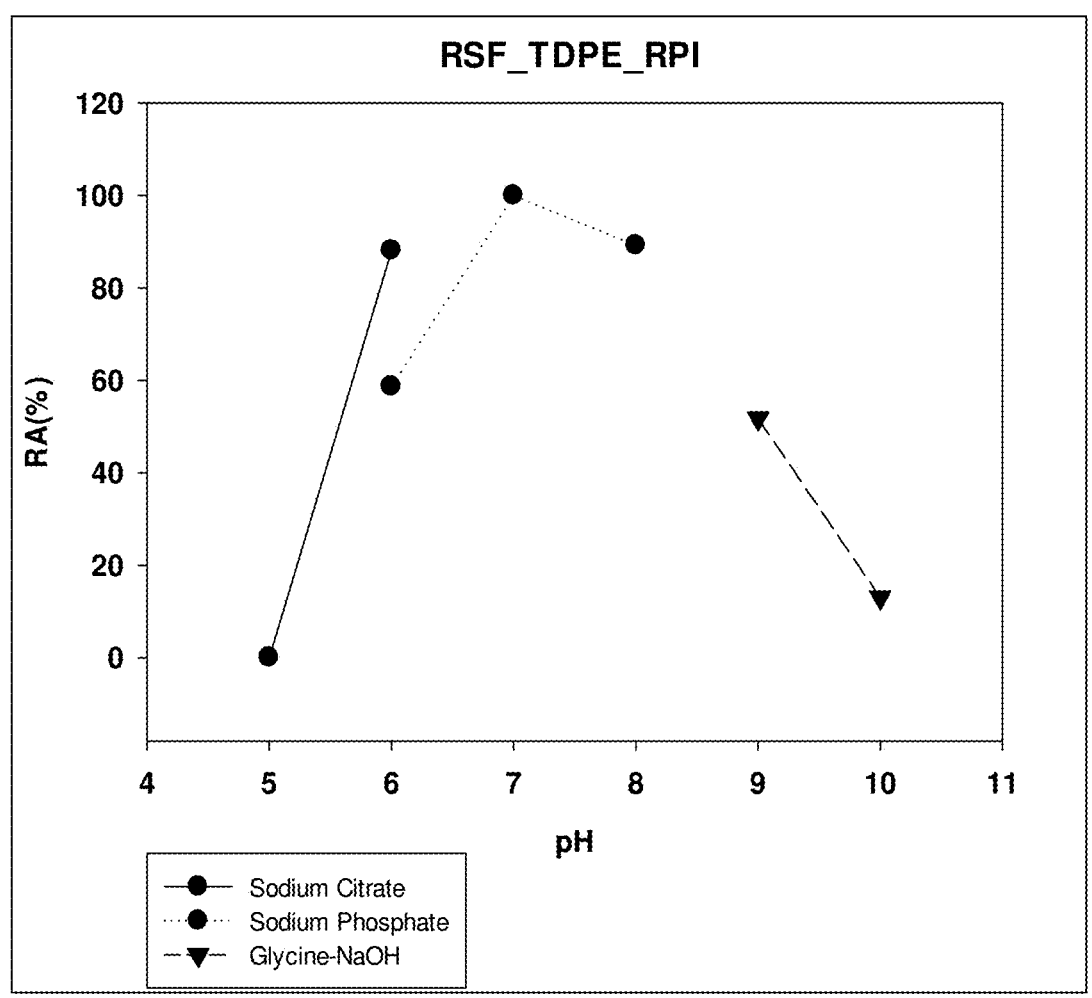

[Fig. 10]
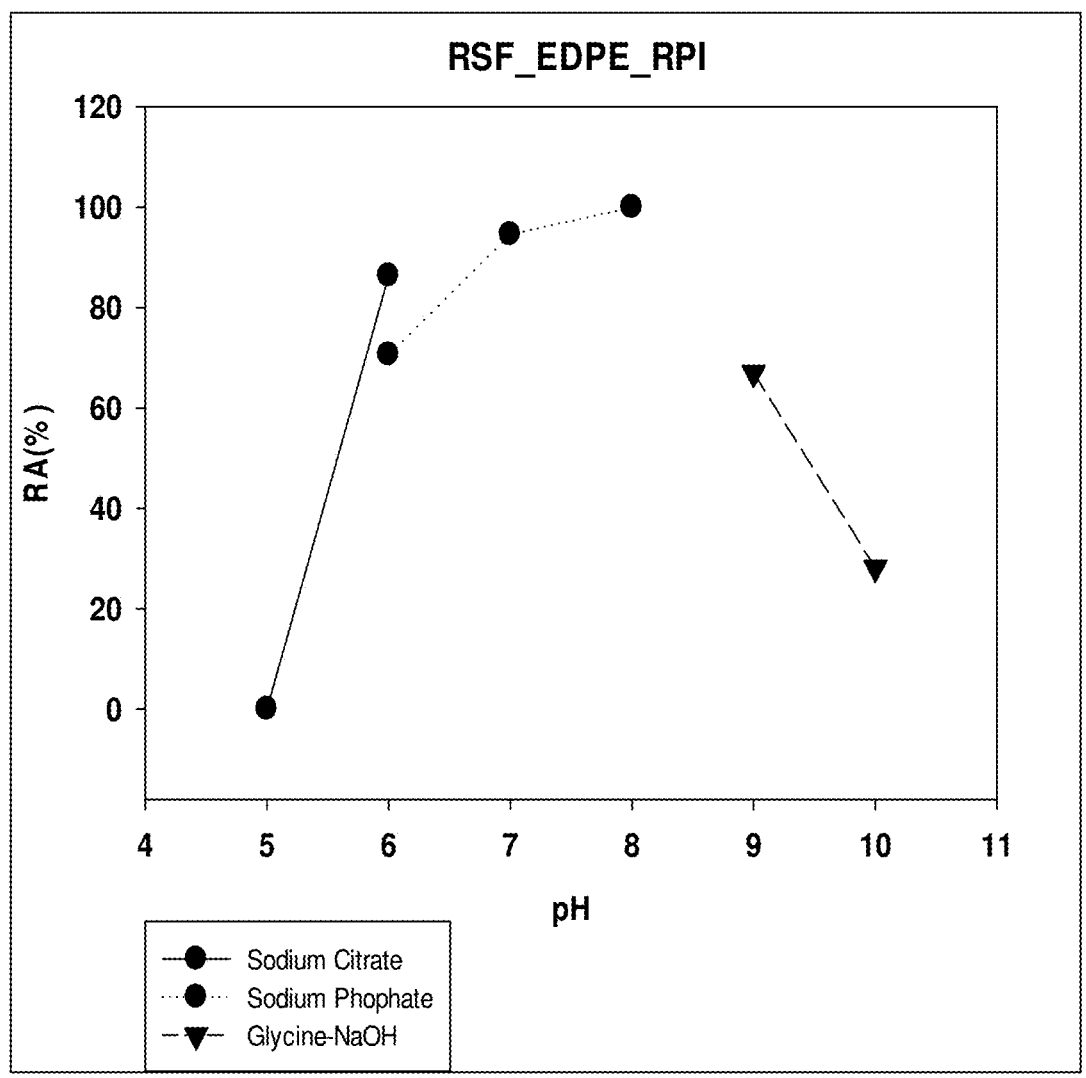

[Fig. 11]
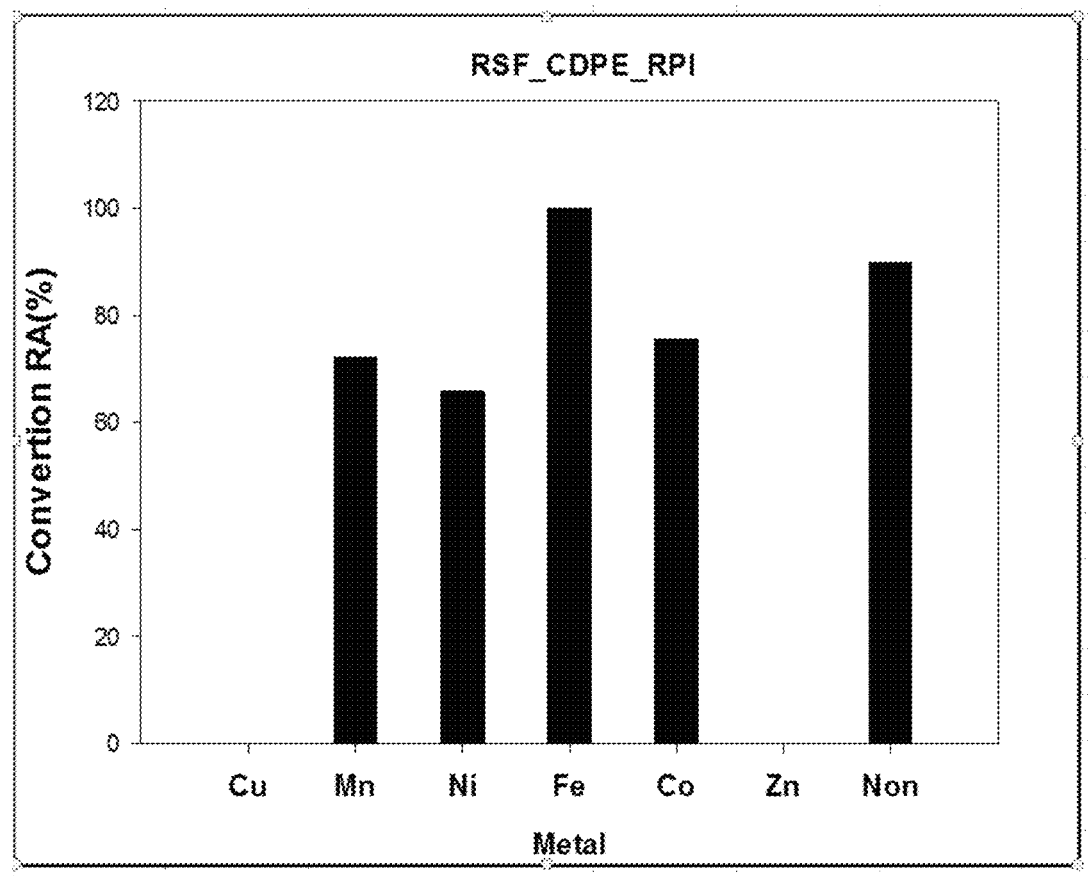

[Fig. 12]
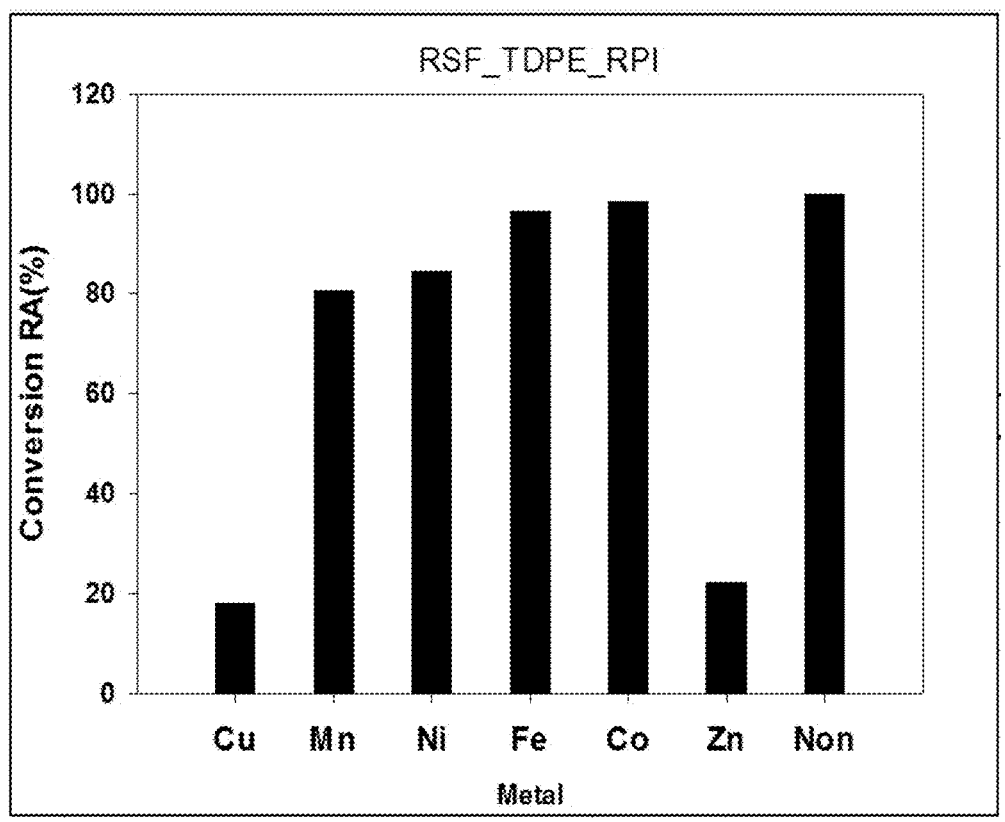

[Fig. 13]
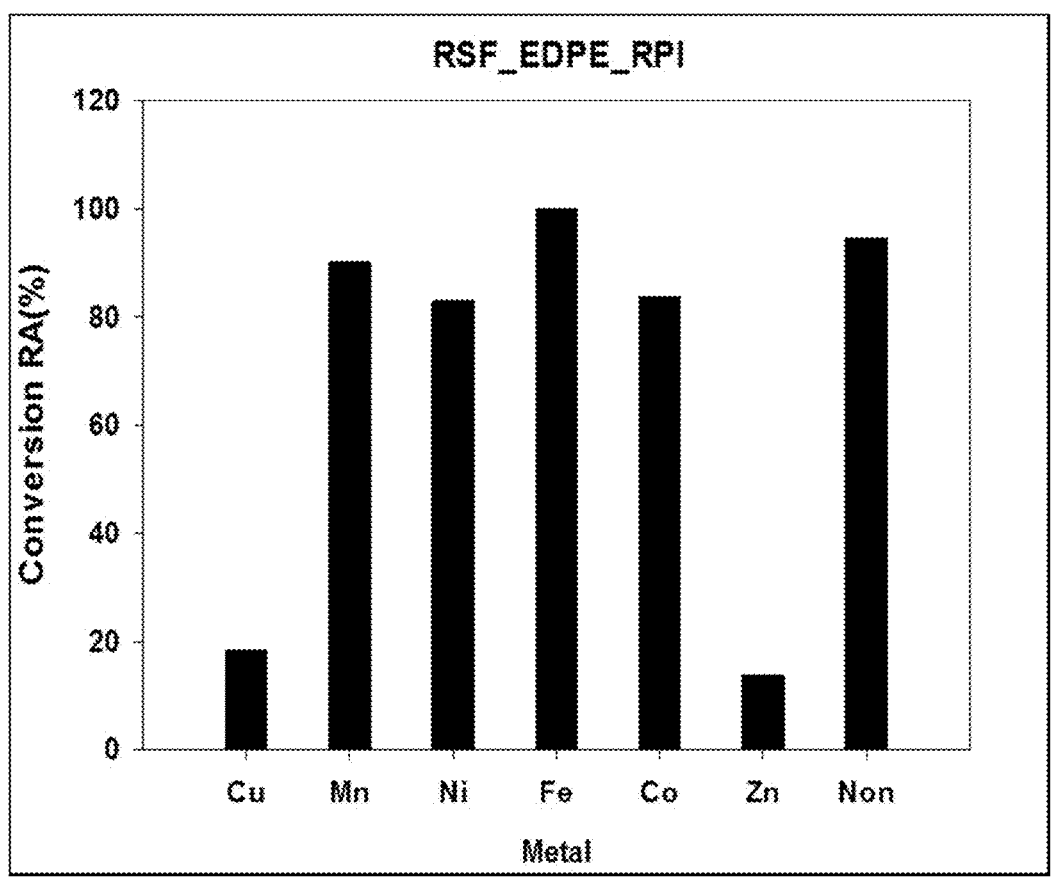

[Fig. 14]
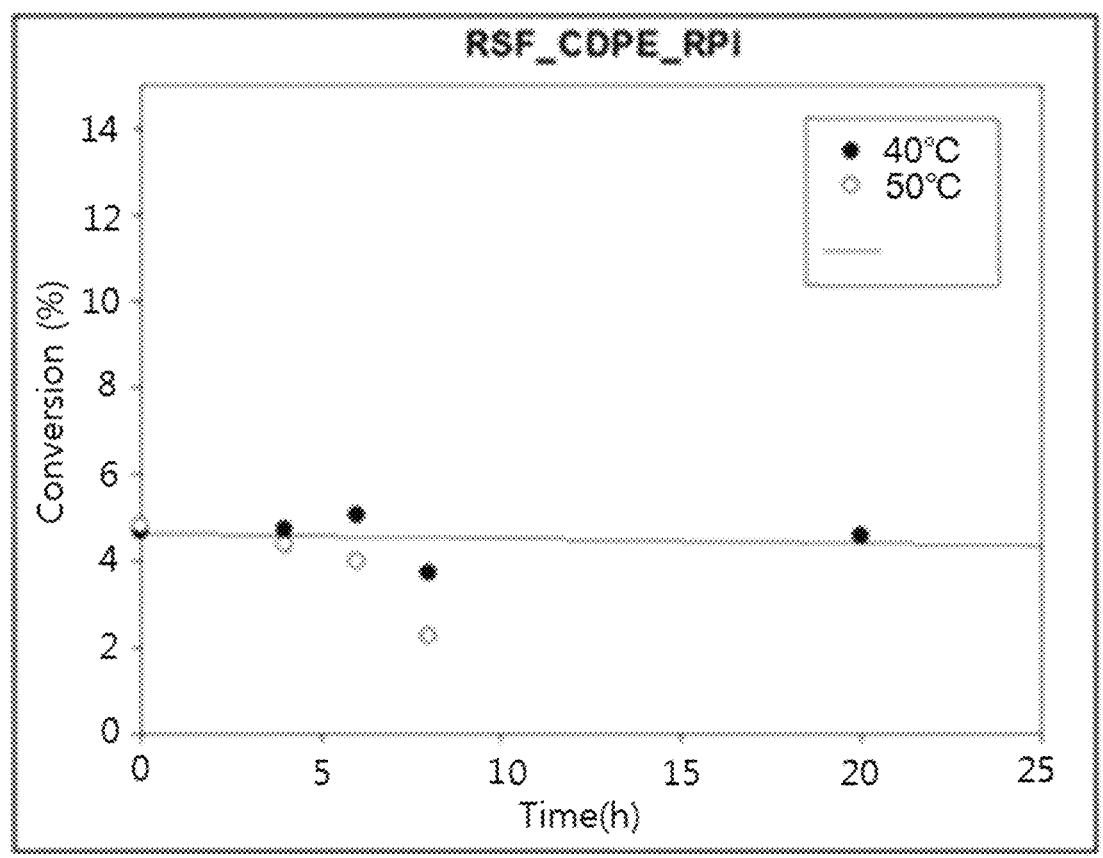

[Fig. 15]
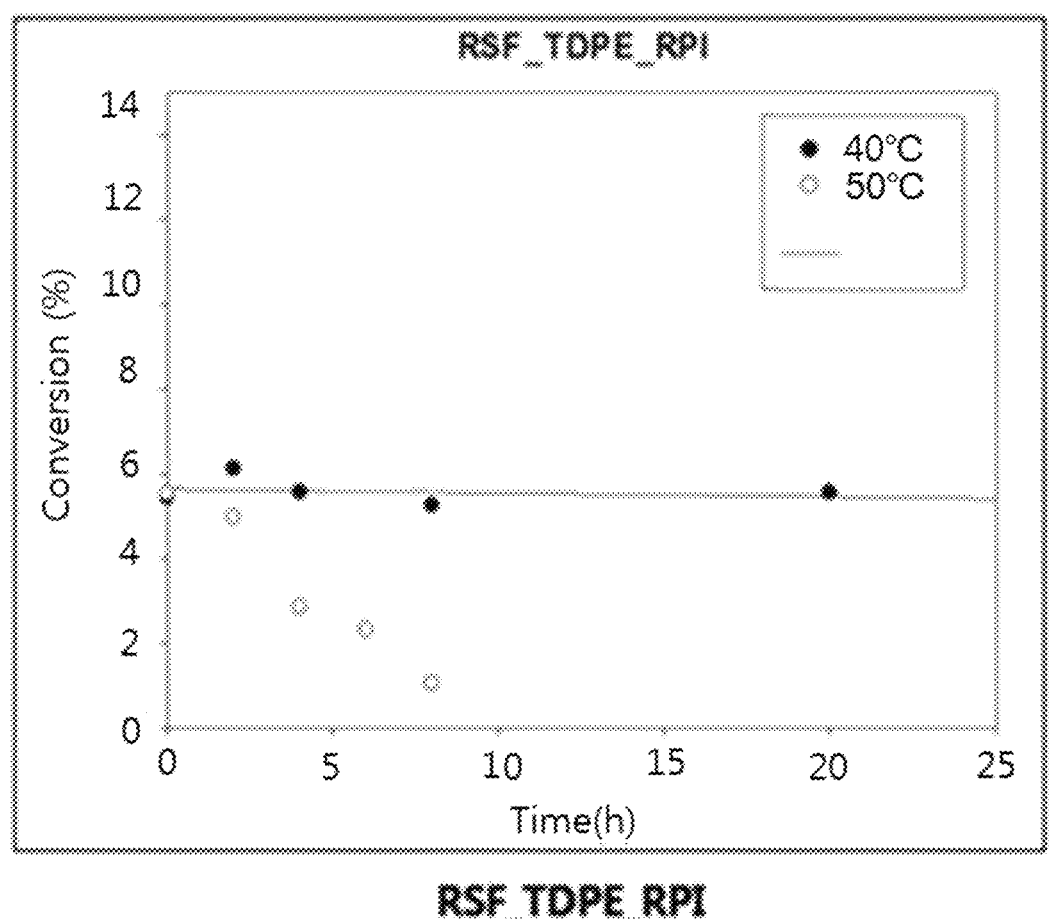

[Fig. 16]
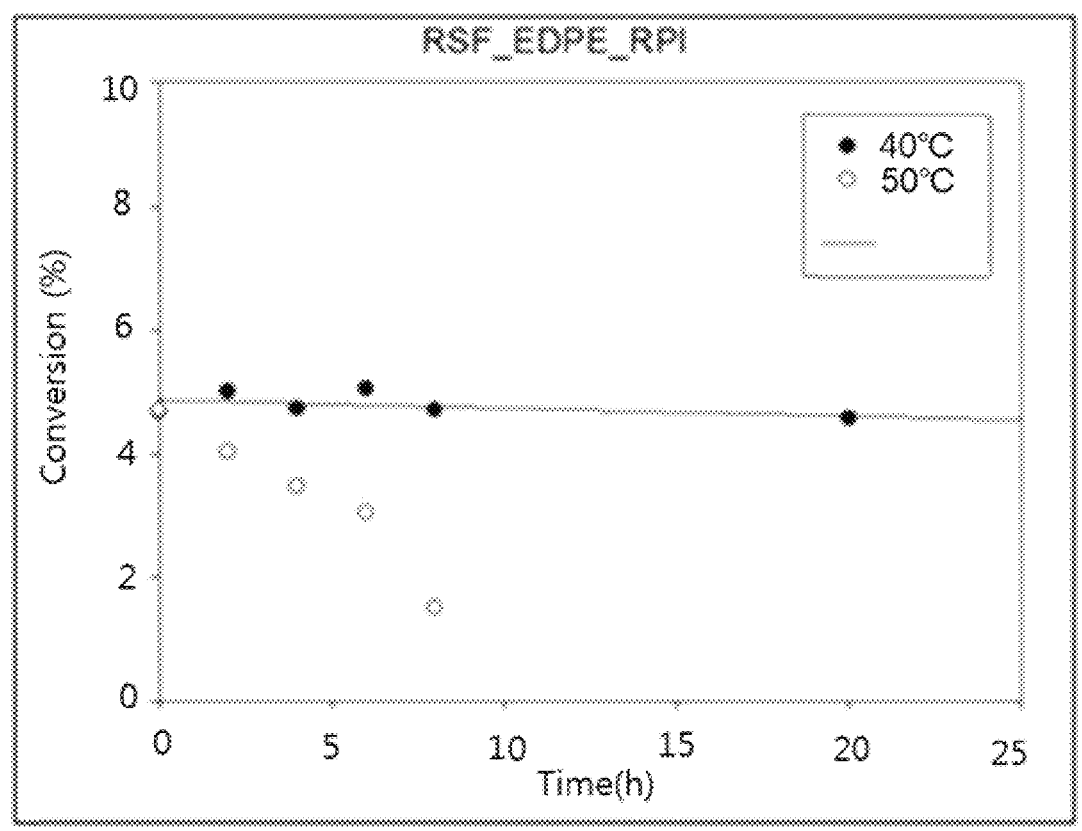
RSF_EDPE_RPI

[Fig. 17]
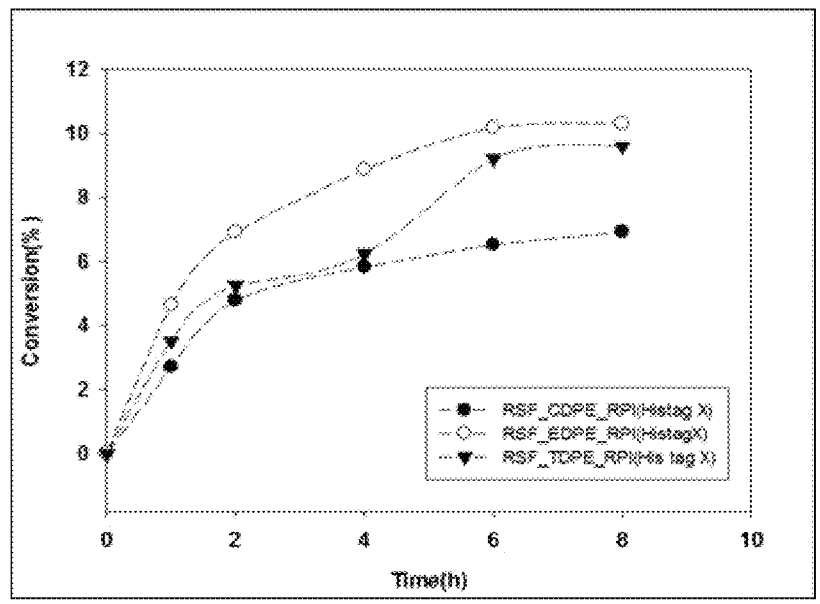
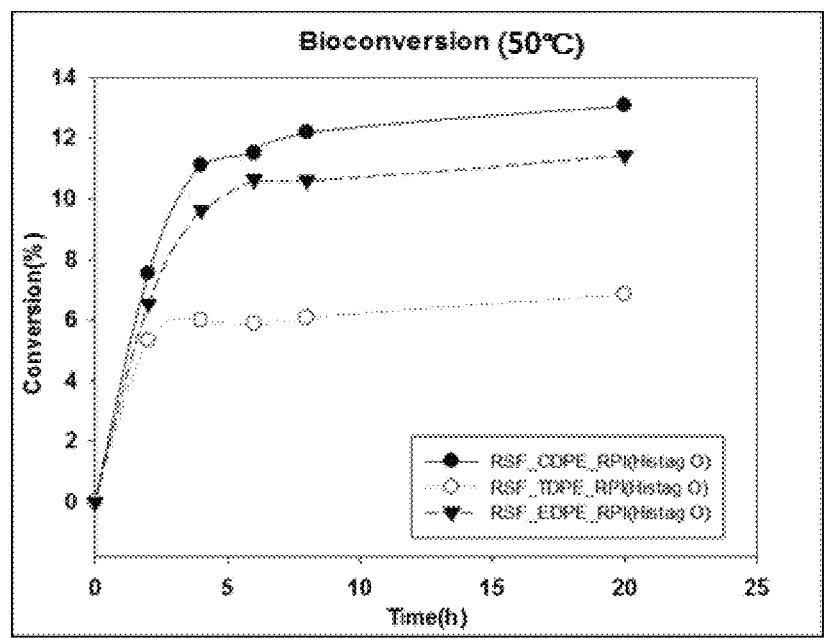

[Fig. 18]
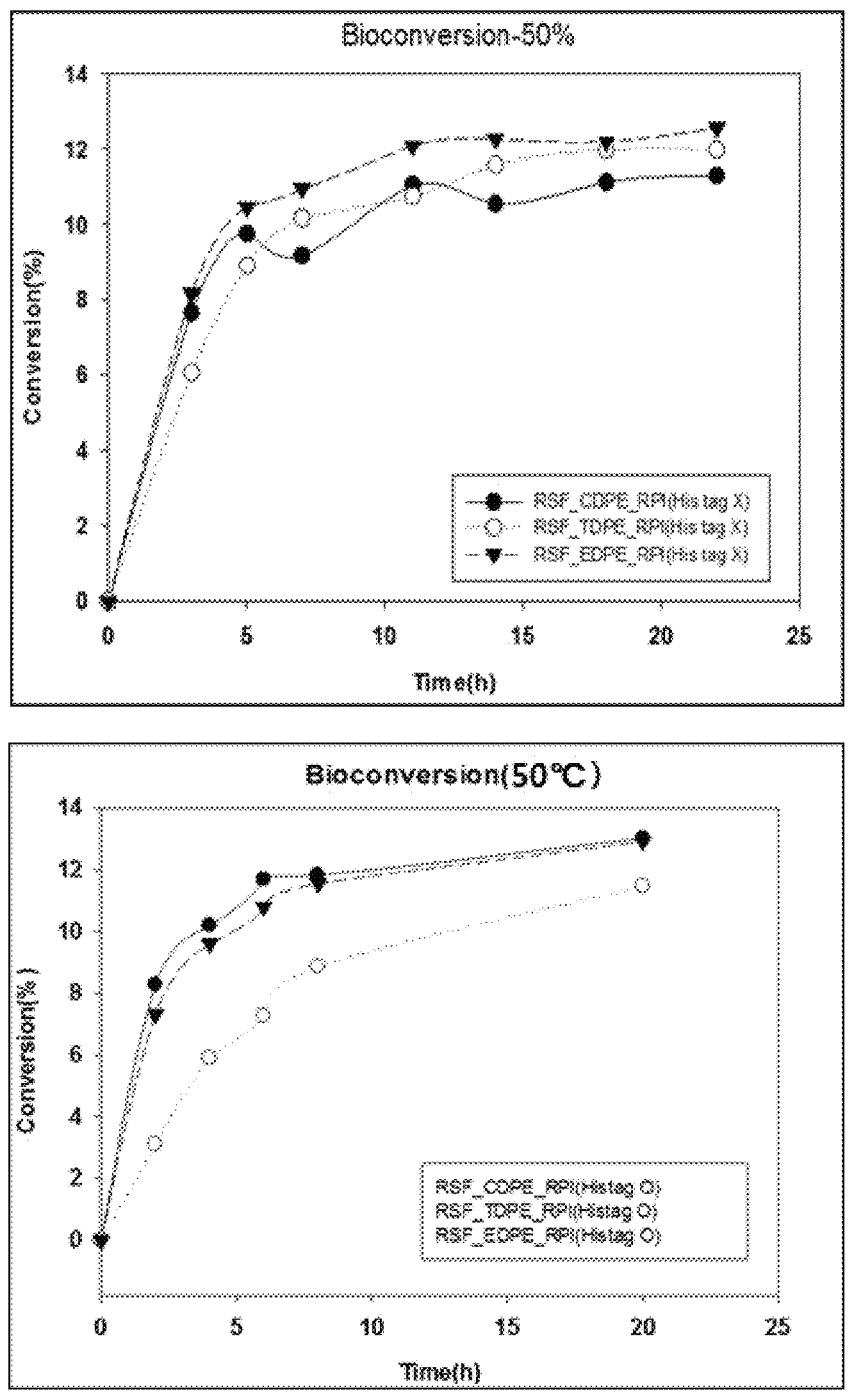

[Fig. 19]
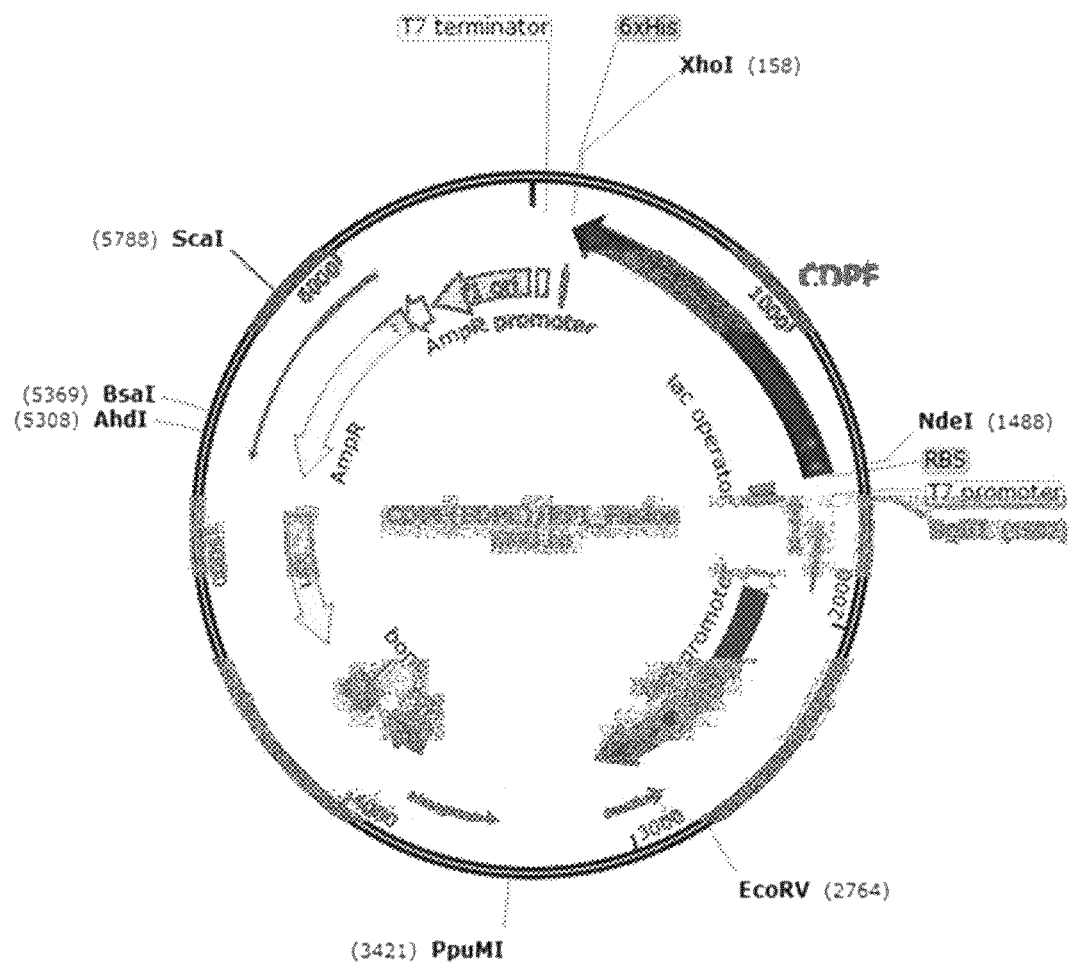

[Fig. 20]
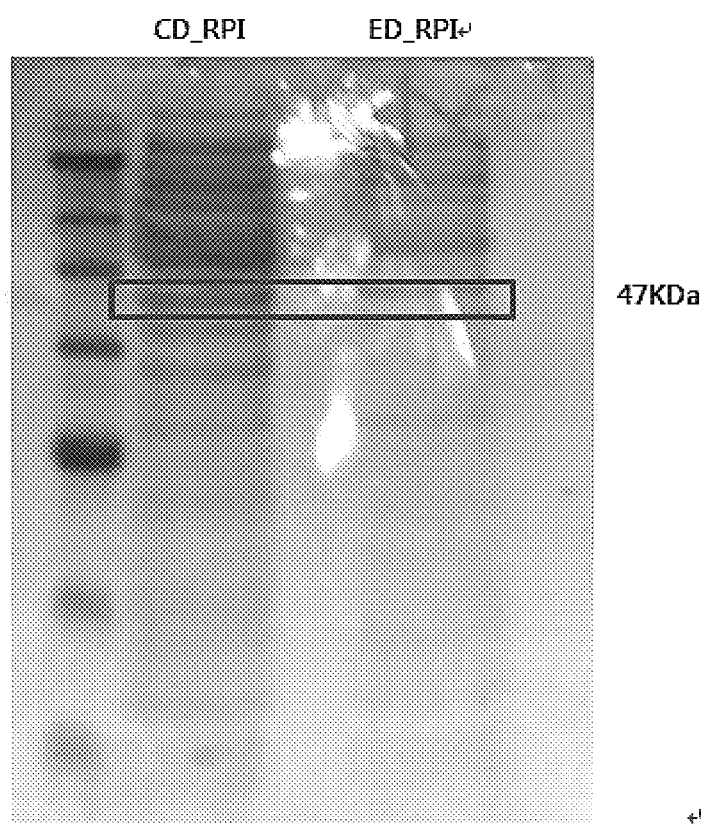

[Fig. 21]
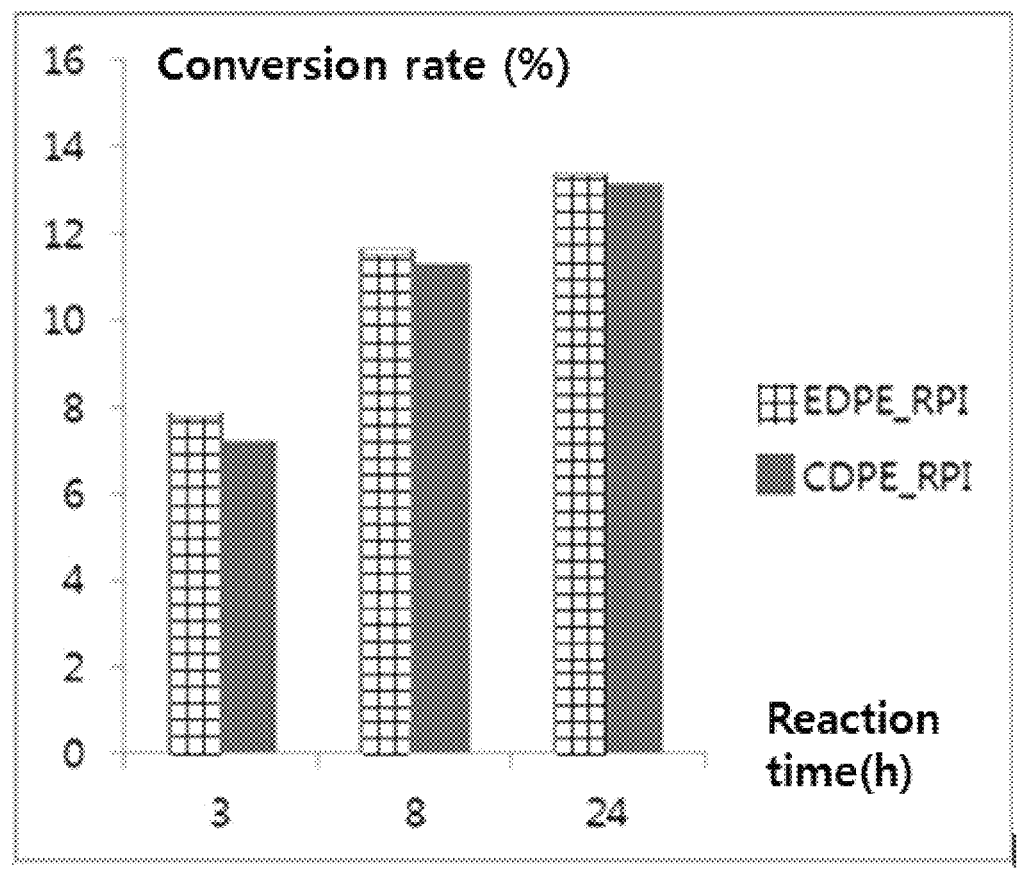

STRAIN PRODUCING ALLOSE FROM FRUCTOSE AND METHOD FOR PRODUCING ALLOSE USING SAME

TECHNICAL FIELD

The present invention relates to a recombinant strain for producing an allose from a fructose, a composition for producing an allose which produces an allose from a fructose-containing raw material comprising the strain, and a method for preparing an allose using the same.

BACKGROUND ART

An allose (D-allose) is a rare sugar monosaccharide known as an isomer of psicose, which is an epimer different from glucose (D-glucose) in the —OH group direction of the 3 carbon. The allose has a function of inhibiting thrombogenesis, autoimmune response of organ transplant patient, and proliferation of cancer cell. In addition, there is an effect of prolonging the death of nerve cell after ischemia of liver and brain, and the research has been conducted as a therapeutic drug for leukemia patients.

Due to the above characteristics, the allose has high utility value as the next generation core material in the medical field, but it is extremely rare in nature, and thus it is needed to develop an efficient production process for industrial application. Conventionally, the allose has been produced mainly by chemical synthesis methods, but there is a problem of production of additional saccharides, and complex purification process due to it and generation of chemical waste in the process.

Therefore, in recent years, a method for producing an allose largely using an enzyme which a microorganism produces has been proposed. Izumori group of Japanese Kagawa University has been reported the production of allose from a psicose using a rhamnose isomerase (L-rhamnose isomerase) from *Pseudomonas stutzeri* (Journal of Fermentation and Bioengineering, 85(5); 539-541, 1998), but the enzyme has a weakness that large amount of altroses (D-altrose) are produced together as by-products during the allose production.

Thus, the development of an enzyme which can exhibit temperature and pH conditions appropriate for industrialization and exhibit high thermal stability without producing by-products as altrose and produce an allose with high yield has been required.

DISCLOSURE

Technical Problem

A purpose of the present invention is to provide a recombinant vector comprising a nucleotide sequence encoding a psicose epimerase and a nucleotide sequence encoding an allose isomerase.

Another purpose of the present invention is to provide a recombinant strain comprising the recombinant vector.

Other purpose of the present invention is to provide a composition for producing an allose comprising one or more kinds selected from the group consisting of the recombinant strain, a culture of the recombinant strain and a lysate of the recombinant strain.

Other purpose of the present invention is to provide a method for producing an allose from a fructose-containing raw material comprising a step of reacting the recombinant strain, a culture of the recombinant strain and a mixture thereof with a fructose-containing raw material.

Other purpose of the present invention is to provide a fusion protein for producing an allose from a fructose comprising an amino acid sequence of SEQ ID NO: 23 or 25.

Other purpose of the present invention is to provide a mixed saccharide composition comprising the fructose, psicose and allose.

Technical Solution

The present invention relates to a recombinant strain for producing an allose from a fructose, a composition for producing an allose which produces an allose from a fructose-containing raw material comprising the strain, and a method for preparing an allose using the same.

Since, when an allose is produced by a conventional chemical synthesis method, there is a problem of production of additional saccharides and complex purification process due to that and generation of chemical waste in the process, and the method using a microorganism has a problem that large amount of altroses (D-altrose) are produced together as by-products during the allose production, it is intended to providing a method for producing an allose which can produce an allose from a fructose with high yield without producing by-products as altrose, exhibiting temperature and pH conditions appropriate for industrialization and exhibiting high thermal stability.

Hereinafter, the present invention will be described in more detail.

Thus, one aspect of the present invention provides a recombinant vector comprising a nucleotide sequence encoding a psicose epimerase and a nucleotide sequence encoding an allose isomerase.

The psicose epimerase may be derived from *Clostridiun scidens*, *Ensifer adhaerens* or *Treponema primitia*.

The psicose epimerase derived from *Clostridiun scidens* (hereinafter, CDPE) is a protein having an activity to produce a psicose from a fructose. For example, the CDPE may have an amino acid sequence of SEQ ID NO: 1 and have an activity to produce a psicose from a fructose. The nucleotide sequence encoding CDPE may comprise a nucleotide sequence encoding a peptide comprising an amino acid sequence of SEQ ID NO: 1, for example, a nucleotide sequence of SEQ ID NO: 5 and/or a nucleotide sequence of SEQ ID NO: 6.

The CDPE may have a molecular weight of monomer measured by sodium dodecyl sulfate polyacrylamide gel electrophoresis (SDS-PAGE) of 30 to 37 kDa, for example, 30 to 35 kDa. The optimum temperature of CDPE may be 40 to 65° C., specifically 50 to 65° C. The optimum temperature may be the result when the reaction is progressed under pH 7.0 and the presence of 1 mM $Co^{2+}$ for 5 minutes, but not limited thereto. In addition, the optimum pH of the protein may be pH 6 to 9, pH 7 to 9, pH 7 to 8.5, or pH 7 to 8. The optimum pH may be the result when the reaction is progressed under 60° C. and the presence of 1 mM $Co^{2+}$ for 5 minutes, but not limited thereto.

The psicose epimerase derived from *Ensifer adhaerens* (hereinafter, EDPE) is a protein having an activity to produce a psicose from a fructose. For example, the EDPE may have an amino acid sequence of SEQ ID NO: 2 and have an activity to produce a psicose from a fructose.

The nucleotide sequence encoding the EDPE may comprise a nucleic acid sequence encoding a peptide comprising an amino acid sequence of SEQ ID NO: 2, for example, a nucleotide sequence of SEQ ID NO: 7.

The psicose epimerase derived from *Treponema primitia* (hereinafter, TDPE) is a protein having an activity to produce a psicose from a fructose. For example, the TDPE may have an amino acid sequence of SEQ ID NO: 3 and have an activity to produce a psicose from a fructose.

The nucleotide sequence encoding the TDPE may comprise a nucleotide sequence encoding a peptide comprising an amino acid sequence of SEQ ID NO: 3, for example, a nucleotide sequence of SEQ ID NO: 8 and/or a nucleotide sequence of SEQ ID NO: 9.

The psicose epimerase may be that a part of amino acid of SEQ ID NO: 1, SEQ ID NO: 2 or SEQ ID NO: 3 is substituted, inserted and/or deleted, as long as the activity to convert a fructose into a psicose is maintained. For example, the psicose epimerase may comprise an amino acid sequence having a homology of 70% or more, 80% or more, 90% or more, 95% or more, or 99% or more to the amino acid sequence of SEQ ID NO: 1, SEQ ID NO: 2 or SEQ ID NO: 3.

The nucleotide sequence encoding the psicose epimerase may be a nucleotide sequence encoding a psicose epimerase obtained from *Clostridiun scidens, Ensifer adhaerens* or *Treponema primitia*, or may be a nucleotide sequence modified to be optimized for expression in *E. coli* or *Corynebacterium* sp. strain.

For example, the nucleotide sequence encoding the psicose epimerase may be a nucleotide sequence coding a peptide comprising an amino acid sequence of SEQ ID NO: 1, a nucleotide sequence coding a peptide comprising an amino acid sequence of SEQ ID NO: 2 or a nucleotide sequence coding a peptide comprising an amino acid sequence of SEQ ID NO: 3.

Specifically, the nucleotide sequence encoding the psicose epimerase may comprise a nucleotide sequence selected from the group consisting of SEQ ID NO: 5 to SEQ ID NO: 9. Otherwise, it may have a nucleotide sequence having a substantial homology to the nucleotide sequence selected from the group consisting of SEQ ID NO: 5 to SEQ ID NO: 9.

The allose isomerase may be derived from *Persephonella marina* EX-H1, and preferably, may be an allose isomerase comprising a peptide comprising an amino acid sequence of SEQ ID NO: 4.

The allose isomerase may be that a part of amino acid of SEQ ID NO: 4 is substituted, inserted and/or deleted, as long as the activity to isomerize a psicose into an allose is maintained. For example, the allose isomerase may comprise an amino acid sequence having a homology of 70% or more, 80% or more, 90% or more, 95% or more, or 99% or more to the amino acid sequence of SEQ ID NO: 4.

The nucleotide sequence encoding the allose isomerase may be a nucleotide sequence encoding an allose isomerase obtained from *Persephonella marina* EX-H1, or may be a nucleotide sequence modified to be optimized for expression in *E. coli* or *Corynebacterium* sp. strain.

For example, the nucleotide sequence encoding the allose isomerase may be a nucleotide sequence coding a peptide comprising an amino acid sequence of SEQ ID NO: 4. For example, it may be a nucleotide comprising a nucleotide sequence of SEQ ID NO: 10. Otherwise, it may comprise a nucleotide sequence having a substantial homology to the nucleotide sequence of SEQ ID NO: 10.

The substantial homology means that the any other nucleotide sequence has a sequence homology of 70% or more, 80% or more, 90% or more, 95% or more, or 99% or more to each nucleotide sequence, by arranging each nucleotide sequence and any other nucleotide sequence to correspond as much as possible and analyzing the sequence.

A person skilled in the art may easily appreciate that a nucleotide sequence encoding an enzyme protein which has a same activity in the range of having the substantial homology by substituting, adding or deleting one or more bases of the nucleotide sequence using a gene recombination technology, etc. known in the art. This comparison of homology may be performed by calculating the honology between 2 or more sequences as a percentage (%) using a commercially available computer program.

The specific amino acid sequences of enzyme according to the present invention are exemplarily described in Table 1, and the nucleotide sequences encoding them are exemplarily described in Tables 2 to 3.

TABLE 1

| SEQ ID NO | Name | Nucleotide sequence (5'→3') |
|---|---|---|
| 1 | CDPE | MKHGIYYAYWEQEWAADYKRYVEKAAKLGFDILEVGAAPLP DYSAQEVKELKKCADDNGIQLTAGYGPAFNHNMGSSDPKIRE EALQWYKRLFEVMAGLDIHLIGGALYSYWPVDFATANKEED WKHSVEGMQILAPIASQYGINLGMEVLNRFESHILNTSEEGVKF VTEVGMDNVKVMLDTFHMNIEESSIGDAIRHAGKLLGHFHTG ECNRMVPGKGRTPWREIGDALREIEYDGTVVMEPFVRMGGQV GSDIKVWRDISKGAGEDRLDEDARRAVEFQRYMLEWK |
| 2 | EDPE | MQGFGVHTSMWTMNWDRPGAERAVAAAVKYAVDFIEIPMLN PPAVDTAHTRALLEKNKLRAVCSLGLPERAWASVRPDAAIEHL KVAIDKTADLGGEALSGVIYGGIGERTGVPPTEAEYDNIARVLQ AAAKHAKTRGIELGVEAVNRYENHLINTGWQAVDMIKRVGA DNVFVHLDTYHMNIEEKGIGTGILDARDFIKYIHLSESDRGTPG YGNCAWDEIFATLAAIGFKGGLAMESFINMPPEVAYGLAVWR PVARDEEEVMGNGLPFLRNKARQYGLI |
| 3 | TDPE | MQYGIYFAYWTKEWQADYKKYIDKVSKLGFDILEISCAALKD QYVSDSQLFDLRDYAKEKGVTLTAGYGPAKGENLSSSDNRVV KNAKAFYKDVLGKLNKLDIRLLGGGLYSYWPVDYSLPIDKAG DWKRSVENIREIAAIAADRNVVLGMEVLNRFEGYLLNTCEEGI KFVDEVNHPNVKVMLDTFHMNIEEDNMAEAIRMAGDKLGHF HIGEQNRKVPGKGCIPWNAIGHALRDIRYNGTVVMEPFVMPG GTIGQDIKVWRNLLPETSETILDRDAKGALEFVKHVFGSTSVL |

TABLE 1-continued

| SEQ ID NO | Name | Nucleotide sequence (5'→3') |
|---|---|---|
| 4 | RPI | MKISIGSDHAGFELKEIIKDHLQKKGYEVVDKGTYSKESVDYPL FGEAVGRSVSEGETDRGIVICGTGIGISISANKIKGVRAALCTNE YMARMSRKHNDANVLALGSRVLGIDLALSIVDTFLSTDFEGGR HERRVHLIQNIEKINL |

TABLE 2

| SEQ ID NO | Name | Nucleotide sequence (5'→3') |
|---|---|---|
| 5 | CDPE (Original) | ATGAAGCATGGTATTTATTACGCGTACTGGGAACAGGAAT GGGCAGCAGATTACAAGCGGTATGTAGAGAAGGCGGCAAA GCTTGGATTCGATATACTGGAGGTTGGCGCGGCGCCACTGC CGGACTATTCTGCGCAGGAGGTAAAGGAACTGAAAAAATG CGCCGATGATAACGGTATCCAGCTGACCGCGGGATATGGT CCCGCCTTCAATCATAATATGGGTTCCTCAGATCCGAAGAT CAGGGAAGAGGCGCTTCAATGGTATAAACGCCTGTTCGAG GTGATGGCAGGCCTTGATATTCATCTGATTGGCGGAGCGCT TTATTCATACTGGCCGGTGGACTTTGCCACAGCCAATAAGG AAGAGGACTGGAAGCACAGCGTGGAGGGAATGCAGATTCT GGCGCCCATCGCCAGCCAGTATGGCATCAATCTGGGAATG GAAGTCCTGAACCGCTTTGAGAGCCATATCTTAAATACTTC GGAAGAAGGCGTGAAGTTCGTGACGGAAGTAGGCATGGAT AATGTGAAAGTCATGCTGGATACGTTCCATATGAACATCGA GGAATCGAGCATTGGCGACGCGATCCGCCATGCCGGGAAA CTTCTTGGACACTTCCACACCGGCGAGTGCAACCGCATGGT ACCCGGAAAGGGCCGCACCCCATGGAGGGAGATCGGGGAT GCCTTGCGCGAGATTGAGTATGACGGAACCGTGGTTATGG AGCCATTTGTACGCATGGGCGGACAGGTAGGCTCTGATATC AAGGTCTGGAGAGACATCAGCAAGGGCGCGGGAGAGGAC CGGCTGGATGAGGATGCAAGGCGCGCGGTAGAGTTCCAGA GATACATGCTTGAATGGAAGTAA |
| 6 | CDPE (E.coli) | ATGAAACACGGTATCTACTACGCGTACTGGGAACAGGAAT GGGCGGCGGACTACAAACGTTACGTTGAAAAAGCGGCGAA ACTGGGTTTCGACATCCTGGAAGTTGGTGCGGCGCCGCTGC CGGACTACTCTGCGCAGGAAGTTAAAGAACTGAAAAAATG CGCGGACGACAACGGTATCCAGCTGACCGCGGGGTTACGGT CCGGCGTTCAACCACAACATGGGTTCTTCTGACCCGAAAAT CCGTGAAGAAGCGCTGCAGTGGTACAAACGTCTGTTCGAA GTTATGGCGGGTCTGGACATCCACCTGATCGGTGGTGCGCT GTACTCTTACTGGCCGGTTGACTTCGCGACCGCGAACAAAG AAGAAGACTGGAAACACTCTGTTGAAGGTATGCAGATCCT GGCGCCGATCGCGTCTCAGTACGGTATCAACCTGGGTATGG AAGTTCTGAACCGTTTCGAATCTCACATCCTGAACACCTCT GAAGAAGGTGTTAAATTCGTTACCGAAGTTGGTATGGACA ACGTTAAAGTTATGCTGGACACCTTCCACATGAACATCGAA GAATCTTCTATCGGTGACGCGATCCGTCACGCGGGTAAACT GCTGGGTCACTTCCACACCGGTGAATGCAACCGTATGGTTC CGGGTAAAGGTCGTACCCCGTGGCGTGAAATCGGTGACGC GCTGCGTGAAATCGAATACGACGGTACCGTTGTTATGGAA CCGTTCGTTCGTATGGGTGGTCAGGTTGGTTCTGACATCAA AGTTTGGCGTGACATCTCTAAAGGTGCGGGTGAAGACCGT CTGGACGAAGACGCGCGTCGTGCGGTTGAATTCCAGCGTT ACATGCTGGAATGGAAATGA |
| 7 | EDPE (Original) | ATGCAGGGTTTTGGCGTCCATACGAGCATGTGGACCATGA ATTGGGATCGCCCCGGTGCGGAGCGCGCCGTTGCGGCGGC GGTAAAATACGCCGTCGACTTCATCGAGATCCCGATGCTCA ATCCGCCGGCGGTTGATACTGCCCATACCAGGCGCTGCTG GAGAAAAACAAGCTGCGCGCGGTCTGCTCGCTCGGCCTGC CGGAGCGCGCCTGGGCATCCGTCCGACCCGATGCCGCGAT CGAGCATCTGAAGGTGGCGATCGACAAGACGGCCGATCTC GGCGGCGAGGCGCTGTCCGGCGTCATCTACGGCGGCATCG GCGAGCGCACCGGCGTGCCGCCGACTGAAGCCGAATACGA CAACATTGCCCGTGTGCTGCAGGCCGCCGCCAAGCACGCC AAAACCCGCGGCATCGAACTGGGTGTCGAGGCGGTCAACC GCTACGAGAACCACCTGATCAACACCGGTTGGCAAGCGGT CGACATGATCAAGCGGGTGGGCGCCGACAATGTCTTCGTG CATCTCGATACCTACCACATGAACATCGAGGAAAAGGGCA TCGGCACCGGCATCCTCGATGCACGCGACTTCATCAAATAC ATCCACCTGTCCGAAAGCGACCGCGGCACGCCCGGCTATG GCAATTGCGCCTGGGACGAGATCTTCGCGACGCTGGCCGC GATCGGTTTCAAGGGTGGGCTGGCGATGGAAAGCTTCATC TABLE 2-continued

| SEQ ID NO | Name | Nucleotide sequence (5'→3') |
|---|---|---|
| | | AACATGCCGCCGGAAGTGGCCTATGGCCTTGCGGTCTGGC GGCCGGTCGCCAGGGACGAAGAGGAAGTGATGGGCAACG GCCTGCCGTTCCTTAGGAACAAGGCCCGGCAATACGGATT GATCTAG |

TABLE 3

| SEQ ID NO | Name | Nucleotide sequence (5'→3') |
|---|---|---|
| 8 | TDPE (Original) | ATGCAATAGGTATTTATTTTGCCTATTGGACAAAGGAATGGCA GGCGGATTACAAAAAGTATATCGATAAAGTATCAAAACTGGGT TTTGATATACTGGAGATATCCTGTGCAGCCTTGAAGGATCAATA TGTTTCGGATTCCCAACTTTTTGATTTGCGGGATTATGCGAAAG AGAAGGGTGTCACCCTGACCGCTGGCTACGGCCCGGCTAAGGG CGAAAATCTTAGTTCTTCCGATAACCGGGTTGTCAAAAATGCA AAAGCCTTTTATAAGGATGTGCTGGGAAAGCTCAACAAACTCG ACATAAGGCTGCTGGGCGGGGGGTTATACTCATACTGGCCGGT TGACTATTCTCTGCCCATTGATAAGGCGGGGGACTGGAAACGG TCAGTTGAAAATATCAGGGAAATTGCCGCAATCGCCGCAGACC GCAACGTGGTATTGGGGATGGAGGTATTAAACCGCTTCGAAGG GTATTTGCTTAACACCTGTGAGGAAGGAATTAAGTTTGTCGATG AAGTTAATCACCCGAATGTAAAAGTCATGCTGGATACTTTTCAC ATGAATATTGAGGAAGATAATATGGCTGAAGCCATCCGCATGG CGGGGGATAAGCTTGGGCATTTTCATATTGGCGAACAGAACCG CAAGGTTCCCGGGAAAGGATGCATCCCCTGGAATGCAATTGGT CATGCCCTGCGGGACATACGGTACAATGGGACGGTGGTGATGG AGCCCTTTGTCATGCCCGGGGGAACCATAGGGCAGGATATAAA AGTCTGGAGAAATTTACTTCCCGAGACAAGCGAAACGATACTG GATCGTGATGCCAAGGGAGCGTTGGAATTTGTGAAGCATGTGT TTGGTAGTACTTCTGTTTTATAA |
| 9 | TDPE (E.coli) | ATGCAGTACGGTATCTACTTCGCGTACTGGACCAAAGAATGGC AGGCGGACTACAAAAAATACATCGACAAAGTTTCTAAACTGGG TTTCGACATCCTGGAAATCTCTTGCGCGGCGCTGAAAGACCAGT ACGTTTCTGACTCTCAGCTGTTCGACCTGCGTGACTACGCGAAA GAAAAAGGTGTTACCCTGACCGCGGGTTACGGTCCGGCGAAAG GTGAAAACCTGTCTTCTTCTGACAACCGTGTTGTTAAAAACGCG AAAGCGTTCTACAAAGACGTTCTGGGTAAACTGAACAAACTGG ACATCCGTCTGCTGGGTGGTGGTCTGTACTCTTACTGGCCGGTT GACTACTCTCTGCCGATCGACAAAGCGGGTGACTGGAAACGTT CTGTTGAAAACATCCGTGAAATCGCGGCGATCGCGGCGGACCG TAACGTTGTTCTGGGTATGGAAGTTCTGAACCGTTTCGAAGGTT ACCTGCTGAACACCTGCGAAGAAGGTATCAAATTCGTTGACGA AGTTAACCACCCGAACGTTAAAGTTATGCTGGACACCTTCCAC ATGAACATCGAAGAAGACAACATGGCGGAAGCGATCCGTATG GCGGGTGACAAACTGGGTCACTTCCACATCGGTGAACAGAACC GTAAAGTTCCGGGTAAAGGTTGCATCCCGTGGAACGCGATCGG TCACGCGCTGCGTGACATCCGTTACAACGGTACCGTTGTTATGG AACCGTTCGTTATGCCGGGTGGTACCATCGGTCAGGACATCAA AGTTTGGCGTAACCTGCTGCCGGAAACCTCTGAAACCATCCTG GACCGTGACGCGAAAGGTGCGCTGGAATTCGTTAAACACGTTT TCGGTTCTACCTCTGTTCTGCTCGAGCACCACCACCACCACCAC TGA |
| 10 | RPI | ATGAAAATCTCTATCGGTTCTGACCACGCGGGTTTCGAACTGAA AGAAATCATCAAAGACCACCTGCAGAAAAAAGGTTACGAAGTT GTTGACAAAGGTACCTACTCTAAAGAATCTGTTGACTACCCGCT GTTCGGTGAAGCGGTTGGTCGTTCTGTTTCTGAAGGTGAAACCG ACCGTGGTATCGTTATCTGCGGTACCGGTATCGGTATCTCTATC TCTGCGAACAAAATCAAAGGTGTTCGTGCGGCGCTGTGCACCA ACGAATACATGGCGCGTATGTCTCGTAAACACAACGACGCGAA CGTTCTGGCGCTGGGTTCTCGTGTTCTGGGTATCGACCTGGCGC TGTCTATCGTTGACACCTTCCTGTCTACCGACTTCGAAGGTGGT CGTCACGAACGTCGTGTTCACCTGATCCAGAACATCGAAAAAA TCAACCTGtAA |

The psicose epimerase and allose isomerase may be one fusion protein connected by a linker peptide.

The psicose epimerase may comprise an amino acid sequence selected from the group consisting of SEQ ID NOs: 1 to 3. In addition, the allose isomerase may comprise an amino acid sequence of SEQ ID NO: 4.

The linker peptide may consist of 1 to 6 amino acids. When the linker peptide has less than or over the number of amino acids, it may negatively affect the structure of proteins each other during connecting two proteins, so the number is suitable.

The one fusion protein may comprise an amino acid sequence of SEQ ID NO: 23 or 25.

In addition, the fusion protein may be encoded by one fusion nucleotide sequence of nucleotide sequence encoding a psicose epimerase and nucleotide sequence encoding an allose isomerase, and said one fusion nucleotide sequence may be a sequence comprising a nucleotide sequence of SEQ ID NO: 22 or SEQ ID NO: 24.

TABLE 4

| SEQ ID NO | Name | Nucleotide sequence (5'->3') |
|---|---|---|
| 22 | EDPE_RPI_FUSION | atgcagggtt ttggcgtcca tacgagcatg tggaccatga attgggatcg ccccggtgcg gagcgcgccg ttgcggcggc ggtaaaatac gccgtcgact tcatcgagat cccgatgctc aatccgccgg cggttgatac tgcccatacc agggcgtgc tggagaaaaa caagctgcgc gcggtctgct cgctcggcct gccggagcgc gcctgggcat ccgtccgacc cgatgccgcg atcgagcatc tgaaggtggc gatcgacaag acggccgatc tcggccggcga ggcgctgtcc ggcgtcatct acggcggcat cggcgagcgc accggcgtgc cgccgactga agccgaatac gacaacattg cccgtgtgct gcaggccgcc gccaagcacg ccaaaacccg cggcatcgaa ctgggtgtcg aggcggtcaa ccgctacgag aaccacctga tcaacaccgg ttggcaagcg gtcgacatga tcaagcgggt gggcgccgac aatgtcttcg tgcatctcga tacctaccac atgaacatcg aggaaaaggg catcggcacc ggcatcctcg atgcacgcga cttcatcaaa tacatccacc tgtccgaaag cgaccgcggc acgcccggct atggcaattg cgcctgggac gagatcttcg cgacgctggc cgcgatcggt ttcaaggggtg ggctggcgat ggaaagcttc atcaacatgc cgccggaagt ggcctatggc cttgcggtct ggcggccggt cgccagggac gaagaggaag tgatgggcaa cggcctgccg ttccttagga caaggcccg gcaatacgga ttgatctcgg gctctggtat gaaaatctct atcggttctg accacgcggg tttcgaactg aaagaaatca tcaaagacca cctgcagaaa aaaggttacg aagttgttga caaaggtacc tactctaaag aatctgttga ctacccgctg ttcggtgaag cggttggtcg ttctgtttct gaaggtgaaa ccgaccgtgg tatcgttatc tgcggtaccg gtatcggtat ctctatctct gcgaacaaaa tcaaaggtgt tcgtgcggcg ctgtgcacca cgaatacat ggcgcgtatg tctcgtaaac acaacgacgc gaacgttctg gcgctgggtt ctcgtgttct gggtatcgac ctggcgctgt ctatcgttga caccttcctg tctaccgact cgaaggtgg tcgtcacgaa cgtcgtgttc acctgatcca gaacatcgaa aaaatcaacc tg |
| 23 | EDPE_RPI_FUSION | MQGFGVHTSMWTMNWDRPGAERAVAAAVKYAVDFIEIPMLNPPAVDTAHTRALLEKNKLRAVCSL GLPERAWASVRPDAAIEHLKVAIDKTADLGGEALSGVIYGGIGERTGVPPTEAEYDNIARVLQAA AKHAKTRGIELGVEAVNRYENHLINTGWQAVDMIKRVGADNVFVHLDTYHMNIEEKGIGTGILDA RDFIKYIHLSESDRGTPGYGNCAWDEIFATLAAIGFKGGLAMESFINMPPEVAYGLAVWRPVARD EEEVMGNGLPFLRNKARQYGLISGSGMKISIGSDHAGFELKEIIKDHLQKKGYEVVDKGTYSKES VDYPLFGEAVGRSVSEGETDRGIVICGTGIGISISANKIKGVRAALCTNEYMARMSRKHNDANVL ALGSRVLGIDLALSIVDTFLSTDFEGGRHERRVHLIQNIEKINL |

TABLE 5

| SEQ ID NO | Name | Nucleotide sequence (5'->3') |
|---|---|---|
| 24 | CDPE_RPI_FUSION | atgaaacacg gtatctacta cgcgtactgg gaacaggaat gggcggcgga ctacaaacgt tacgttgaaa aagcggcgaa actgggtttc gacatcctgg aagttggtgc ggcgccgctg ccggactact ctgcgcagga agttaaagaa ctgaaaaaat gcgcggacga caacggtatc cagctgaccg cgggttacgg tccggcgttc aaccacaaca tggttcttc tgacccgaaa atccgtgaag aagcgctgca gtggtacaaa cgtctgttcg aagttatggc gggtctggac atccacctga tcggtggtgc gctgtactct tactggccgg ttgacttcgc gaccgcgaac aaagaagaag actggaaaca ctctgttgaa ggtatgcaga tcctggcgcc gatcgcgtct cagtacggta tcaacctggg tatggaagtt ctgaaccgtt tcgaatctca catcctgaac acctctgaag aaggtgttaa attcgttacc gaagttggta tggacaacgt taagttatg ctggacacct tccacatgaa catcgaagaa tcttctatcg gtgacgcgat ccgtcacgcg ggtaaactgc tgggtcactt ccacaccggt gaatgcaacc gtatggttcc gggtaaaggt cgtaccccgt ggcgtgaaat cggtgacgcg ctgcgtgaaa tcgaatacga cggtaccgtt gttatggaac cgttcgttcg tatgggtggt caggttggtt ctgacatcaa agtttggcgt gacatctcta aaggtgcggg tgaagaccgt ctggacgaag acgcgcgtcg tgcggttgaa ttccagcgtt acatgctgga atggaaatcg ggctctgata tgaaaatctc tatcggttct gaccacgcgg gtttcgaact gaaagaaatc atcaaagacc acctgcagaa aaaaggttac gaagttgttg acaaaggtac ctactctaaa gaatctgttg actacccgct gttcggtgaa gcggttggtc gttctgtttc tgaaggtgaa accgaccgtg gtatcgttat ctgcggtacc ggtatcggta tctctatctc tgcgaacaaa atcaaaggtg ttcgtgcggc gctgtgcacc aacgaataca tggcgcgtat gtctcgtaaa cacaacgacg cgaacgttct ggcgctgggt tctcgtgttc tgggtatcga cctggcgctg tctatcgttg acaccttcct gtctaccgac ttcgaaggtg gtcgtcacga acgtcgtgtt cacctgatcc agaacatcga aaaaatcaac ctgtaa |
| 25 | CDPE_RPI_FUSION | MKHGIYYAYWEQEWAADYKRYVEKAAKLGFDILEVGAAPLPDYSAQEVKELKKCADDNGIQLTAG YGPAFNHNMGSSDPKIREEALQWYKRLFEVMAGLDIHLIGGALYSYWPVDFATANKEEDWKHSVE GMQILAPIASQYGINLGMEVLNRFESHILNTSEEGVKFVTEVGMDNVKVMLDTFHMNIEESSIGD AIRHAGKLLGHFHTGECNRMVPGKGRTPWREIGDALREIEYDGTVVMEPFVRMGGQVGSDIKVWR DISKGAGEDRLDEDARRAVEFQRYMLEWKSGSGMKISIGSDHAGFELKEIIKDHLQKKGYEVVDK GTYSKESVDYPLFGEAVGRSVSEGETDRGIVICGTGIGISISANKIKGVRAALCTNEYMARMSRK HNDANVLALGSRVLGIDLALSIVDTFLSTDFEGGRHERRVHLIQNIEKINL |

The recombinant vector may be constructed as a vector for cloning or vector for expression by a method widely known in the art (Francois Baneyx, current Opinion Biotechnology 1999, 10:411-421). All vectors used for gene recombination may be used, and for example, the recombinant vector may be selected from the group consisting of plasmid expression vector, virus expression vector (e.g. replication defective retrovirus, adenovirus, and adeno-associated virus) and virus vector which can perform an equivalent function thereto, etc., but not limited thereto.

For example, the recombinant vector may be constructed from one selected from the group consisting of pACYC, RSF, pET, pKK223-3, pTrc99a, pKD, pXMJ19, pCES208 vectors, etc., and preferably, may be pACYC or RSF.

The recombinant vector means a recombinant nucleic acid molecule which can deliver a target polynucleotide connected to be operational, and the target polynucleotide may be operationally connected with one or more transcriptional regulatory factors consisting of promoter and transcription termination factor.

The transcription termination factor may be rrnB, rrnB_T1, rrnB_T2, T7 terminator, etc., and preferably, may be T7 transcription termination factor after PCR from pET21a vector.

Another aspect of the present invention relates to a recombinant strain transformed with the recombinant vector.

The cleavage maps of specific recombinant vectors according to the present invention are exemplarily described in FIG. 1 to FIG. 4.

As a method for transforming a host cell with the recombinant vector, all transformation methods known in the art may be selected and used without special limitation, and for example, may be selected from fusion of bacterial protoplasts, electroporation, projectile bombardment and infection using a virus vector, etc.

The transformed recombinant strain according to the present invention can have high stability and overexpress introduced psicose epimerase and allose isomerase, and thus can provide stably high allose conversion activity for a long period. Therefore, the transformed recombinant strain may be usefully applied for preparation of allose and may further enhance allose production yield.

Culturing the recombinant strain may be performed in an appropriate medium by various culturing methods known in the art. For examples of the culturing methods, batch culturing, continuous culturing and fed-batch culturing are included. The fed-batch culturing includes fed batch and repeated fed batch culturing, but not limited thereto.

The medium which can be used according to the present invention comprises one or more carbon sources, nitrogen sources, mineral salt, vitamin, and(or) trace elements. Preferable carbon source is a saccharide such as monosaccharides, disaccharides or polysaccharides. The nitrogen source is generally an organic or inorganic nitrogen compound or a material comprising the compound. As an example of nitrogen sources, there is ammonia gas or ammonium salt, for example, ammonium sulfate, ammonium chloride, ammonium phosphate, ammonium carbonate or ammonium nitrate, nitrate, urea, amino acid or complex nitrogen sources, for example, corn steep liquor, soybean powder, soybean protein, yeast extract, meat extract, etc. The nitrogen source may be used alone or as a mixture.

The inorganic salt compound that may be present in the medium comprises a chloride, phosphate or sulfate of calcium, magnesium, sodium, cobalt, molybdenum, potassium, manganese, zinc, copper and iron. As a phosphorus source, phosphoric acid, potassium dihydrogen phosphate or dipotassium hydrogen phosphate, or corresponding sodium-containing salt may be used. In order to maintain a metal ion in a solution, a chelating agent may be added into the medium. All components of medium are sterilized by heating (at 1.5 bar and 121° C. for 20 minutes) or sterile filtration. These components may be sterilized together or individually as needed. All components of medium may be present when the culturing starts, or discretionally be added continuously or in batch.

Other aspect of the present invention provides a composition for producing an allose comprising a microbial cell of the recombinant strain and/or culture of recombinant strain.

The composition may prepare an allose from a fructose-containing raw material. In addition, the culture may comprise an enzyme produced from the recombinant strain, and it may comprise the strain or be a cell-free form which does not comprise the strain.

Herein, unless otherwise stated, the recombinant strain used for the preparation of allose is used to mean a microbial cell of the strain and/or culture of the strain.

For the composition for producing an allose, the allose may be a form of saccharide composition consisting of fructose, psicose and allose, and for example, may be a form of mixed saccharide composition comprising 60 to 63% by weight of fructose, 24 to 26% by weight of psicose, and 12 to 15% by weight of allose, based on 100% by weight of saccharide composition consisting of fructose, psicose and allose.

The composition may produce an allose from a fructose with a conversion rate of 12% or more, for example, 12 to 15%, 12 to 14% or 12 to 13%. In case of passing through a 2-step process for producing an allose from a psicose, after producing a psicose from a fructose, the allose is produced with a conversion rate of about 9%, and a problem that it takes a long time and increases the production cost occurs, because it cannot produce it through one process. However, in case of producing an allose using the composition, since the allose can be produced through a 1-step process, the time is shorten and the production cost may be reduced, and particularly the allose may be produced with 30% or more enhanced yield than the case of producing it through the 2-step process.

The composition may not comprise one or more metal ions selected from the group consisting of copper ion, manganese ion, calcium ion, magnesium ion, zinc ion, nickel ion, cobalt ion, iron ion, aluminum ion, and calcium ion.

Other aspect of the present invention provides a method for producing an allose by contacting the composition for producing an allose comprising the microbial cell of the recombinant strain and/or culture of the recombinant strain with a fructose-containing raw material.

The method for producing an allose comprises a step of reacting the recombinant strain with a fructose-containing raw material. In one specific embodiment, the step of reacting the recombinant strain with a fructose may be performed by a step of culturing the microbial cell of the recombinant strain in a culture medium comprising a fructose. In other specific embodiment, the step of reacting the recombinant strain with a fructose may be performed by a step of contacting the recombinant strain (microbial cell and/or culture of strain) with a fructose, for example, a step of mixing the recombinant strain with a fructose or a step of contacting a fructose into a carrier in which the recombinant strain is immobilized. As such, a fructose may be converted into a psicose by reacting the recombinant strain with a fructose, and the psicose may be converted into an allose, thereby producing an allose from a fructose.

For the method for producing an allose, the allose may be a form of saccharide composition consisting of fructose, psicose and allose, and for example, may be a mixed saccharide composition comprising 60 to 63% by weight of fructose, 24 to 26% by weight of psicose, and 12 to 15% by weight of allose, based on 100% by weight of saccharide composition consisting of fructose, psicose and allose.

In addition, the method may produce an allose from a fructose with a conversion rate of 12% or more, for example, 12 to 15%, 12 to 14% or 12 to 13%.

In addition, for the method for producing an allose, the concentration of fructose used as a substrate for efficient psicose production may be 10 to 80% (w/v), 20 to 30% (w/v), 40 to 80% (w/v), 10 to 75% (w/v), 20 to 75% (w/v), 30 to 75% (w/v), for example, 40 to 75% (w/v), based on the total reactants. When the concentration of fructose is lower than the range, economics are lowered, and when it is higher than the range, the fructose is not dissolved well, and therefore, the concentration of fructose in the range is preferable. The fructose may be used as a liquid state dissolved in a buffer solution or water (for example, distilled water).

For the method for producing an allose, the reaction may be performed under the condition of pH 6 to 9, for example, pH 7 to 9, pH 7 to 8 or pH 8 to 9. In addition, the reaction may be performed under the temperature condition of 30° C. or higher, for example 40° C. or higher. When the temperature becomes 80° C. or more, the browning reaction of fructose that is a substrate may be occurred, and therefore, the reaction may be performed under the condition of 30 to 80° C., for example, 35 to 80° C., 40 to 80° C., 35 to 75° C., 40 to 75° C., 35 to 70° C. or 40 to 70° C.

In addition, for the production method, as longer the reaction time is, the higher the allose conversion rate is. For example, the reaction time is preferably 1 hr or more, for example, 2 hrs or more, 3 hrs or more, 4 hrs or more, 5 hrs or more or 6 hrs or more. When the reaction time is over 48 hours, the rate of increase of allose conversion rate is slight or rather decreased, and therefore the reaction time is preferably not over 48 hours. Thus the reaction time may be 1 to 48 hours, 2 to 48 hours, 3 to 48 hours, 4 to 48 hours, 5 to 48 hours, or 6 to 48 hours, and considering industrial and economical aspects, may be approximately 1 to 48 hours, 2 to 36 hours, 3 to 24 hours, 3 to 12 hours, or 3 to 6 hours, but not limited thereto. The condition is selected as a condition to maximize the conversion efficiency of allose from a fructose.

In addition, for the allose production method, the concentration of microbial cell of recombinant strain used may be 5 mg (dcw: dry cell weight)/ml or more, for example, 5 to 100 mg(dcw)/ml, 10 to 90 mg(dcw)/ml, 20 to 80 mg(dcw)/ml, 30 to 70 mg(dcw)/ml, 40 to 60 mg(dcw)/ml, or 45 to 55 mg(dcw)/ml based on the total reactants. When the concentration of microbial cell is less than the range, the activity of allose conversion is low or little, and when it is over the range, microbial cells are too many, and thus the total efficiency of allose conversion reaction is lowered, and therefore, the concentratin of microbial cell is preferably in the range.

In addition, for the allose production method, the method may not add one or more kinds of metal ions selected from the group consisting of copper ion, manganese ion, calcium ion, magnesium ion, zinc ion, nickel ion, cobalt ion, iron ion, aluminum ion, and calcium ion.

Other aspect of the present invention provides an enzyme for producing an allose from a fructose comprising a fusion protein in which a psicose epimerase and an allose isomerase are connected by a linker peptide.

The enzyme is characterized by producing an allose from a fructose with a conversion rate of 12% or more, for example, 12 to 15%, 12 to 14% or 12 to 13%.

In addition, the psicose epimerase may comprise an amino acid sequence selected from the group consisting of SEQ ID NO: 1 to 3. In addition, the allose isomerase may comprise an amino acid sequence of SEQ ID NO: 4.

The linker peptide may consist of 1 to 6 amino acids. When the linker peptide is less than or over the number of amino acids, it may negatively affect the structure of proteins each other during connecting two proteins, so the number is suitable.

The one fusion protein may comprise an amino acid sequence of SEQ ID NO: 23 or 25.

Other aspect of the present invention provides a mixed saccharide composition comprising 60 to 63% by weight of fructose, 24 to 26% by weight of psicose, and 12 to 15% by weight of allose, based on 100% by weight of saccharide composition consisting of fructose, psicose and allose.

Effect of the Invention

The present invention relates to a recombinant strain for producing an allose from a fructose, a composition for producing an allose, which produces an allose from a fructose-containing raw material, comprising the recombinant strain, and a method for producing an allose using the same, and by using the recombinant strain and/or method for producing an allolse using the same according to the present invention, an allose can be produced with high yield, without producing by-products, exhibiting temperature and pH conditions appropriate for industrialization and exhibiting high thermal stability.

BRIEF DESCRIPTION OF DRAWINGS

FIG. 1 shows a cleavage map of recombinant vector in which CDPE or TDPE and RPI genes are introduced into pACYCDuet-1 vector according to one example of the present invention.

FIG. 2 shows a cleavage map of recombinant vector in which EDPE and RPI genes are introduced into pACYCDuet-1 vector according to one example of the present invention.

FIG. 3 shows a cleavage map of recombinant vector in which CDPE or TDPE and RPI genes are introduced into RSFDuet-1 vector according to one example of the present invention.

FIG. 4 shows a cleavage map of recombinant vector in which EDPE and RPI genes are introduced into RSFDuet-1 vector according to one example of the present invention.

FIG. 5 is a graph showing the result of cell reaction activity analysis by temperature of RSF_CDPE_RPI strain according to one example of the present invention.

FIG. 6 is a graph showing the result of cell reaction activity analysis by temperature of RSF_TDPE_RPI strain according to one example of the present invention.

FIG. 7 is a graph showing the result of cell reaction activity analysis by temperature of RSF_EDPE_RPI strain according to one example of the present invention.

FIG. 8 is a graph showing the result of cell reaction activity analysis by pH of RSF_CDPE_RPI strain according to one example of the present invention.

FIG. 9 is a graph showing the result of cell reaction activity analysis by pH of RSF_TDPE_RPI strain according to one example of the present invention.

FIG. 10 is a graph showing the result of cell reaction activity analysis by pH of RSF_EDPE_RPI strain according to one example of the present invention.

FIG. 11 is a graph showing the result of analysis of metal ion requirement of enzyme in RSF_CDPE_RPI strain according to one example of the present invention.

FIG. 12 is a graph showing the result of analysis of metal ion requirement of enzyme in RSF_TDPE_RPI strain according to one example of the present invention.

FIG. 13 is a graph showing the result of analysis of metal ion requirement of enzyme in RSF_EDPE_RPI strain according to one example of the present invention.

FIG. 14 is a graph showing the result of analysis of cell reaction thermal stability of RSF_CDPE_RPI strain according to one example of the present invention.

FIG. 15 is a graph showing the result of analysis of cell reaction thermal stability of RSF_TDPE_RPI strain according to one example of the present invention.

FIG. 16 is a graph showing the result of analysis of cell reaction thermal stability of RSF_EDPE_RPI strain according to one example of the present invention.

FIG. 17 is a graph showing the result of allose production from 15% fructose according to one example of the present invention.

FIG. 18 is a graph showing the result of allose production from 50% fructose according to one example of the present invention.

FIG. 19 is a cleavage map of recombinant vector in which CDPE or TDPE and RPI genes are fused into pACYCDuet-1 vector according to one example of the present invention.

FIG. 20 is a photograph confirming the expression of fusion enzyme according to one example of the present invention through SDS-PAGE.

FIG. 21 is a graph showing the result of measuring the allose conversion rate of fusion enzyme according to one example of the present invention.

DETAILED DESCRIPTION OF THE EMBODIMENTS

Hereinafter, the present invention will be described in more detail by the following examples. However, these examples are only for illustrating the present invention, and the scope of the present invention is not limited by these examples.

Example 1. Preparation of Duet Plasmid and Transformation

Plasmids for expressing enzyme for producing a psicose from a fructose, CDPE, EDPE, or TDPE each, in one strain, with RPI enzyme for producing an allose from a psicose was constructed through gene recombination.

Specifically, in order to prepare a vector introducing a sequence encoding RPI, a recombinant vector was prepared by inserting the polynucleotide encoding the amino acid sequence of SEQ ID NO: 4 which was a RPI protein (SEQ ID NO; 11) into a same restriction enzyme site of pACYC (NOVAGEN) or RSF (NOVAGEN) which was an expression vector using NdeI and XhoI(NEB).

Then, to prepare a vector introducing a sequence encoding the psicose epimerase, a sequence encoding psicose epimerase was prepared first.

Specifically, as the polynucleotide encoding the amino acid sequence of SEQ ID NO: 1 derived from *Clostridiuim scindens* (Gene bank: EDS06411.1), polynucleotide encoding the amino acid sequence of SEQ ID NO: 2 derived from *Ensifer adhaerens* or polynucleotide encoding the amino acid sequence of SEQ ID NO: 3 derived from *Treponema primitia* (Gene bank: WP_010256447), to be optimized for *E. coli* to be used as an expression strain, original nucleotide sequences of encoding polynucleotides (SEQ ID NOs: 5, 7 and 8, respectively) and polynucleotides modified thereof were synthesized by requesting to Bioneer. Co (Korea).

Then, by using restriction enzymes NdeI and XhoI(NEB), the synthesized polynucleotides encoding each psicose epimerase was inserted into same restriction site of pACYC (NOVAGEN) or RSF(NOVAGEN) which was an expressing vector in which RPI gene was inserted, and TDPE, CDPE, EDPE were respectively inserted into the prepared recombinant vector comprising RPI, to make two genes (RPI enzyme gene and psicose epimerase gene) be inserted into one vector. The restriction enzymes were shown in the following Table 6.

TABLE 6

| SEQ ID NO | Primer Name | Nucleotide Sequence (5'→3') | Restriciton Enzyme |
|---|---|---|---|
| 11 | CDPE_F_BamHI(Duet) | CGATCGGATCCGATGAAACACG GTATCTACTAC | BamHI |
| 12 | CDPE_R_HindIII(Duet) | GCGACCAAGCTTTTATTTCCATT CCAGCATG | HindIII |
| 13 | EDPE_F_BamHI(Duet) | CGATCGGATCCGATGCAGGGTTT TGGCGTC | BamHI |
| 14 | EDPE_R_NotI(Duet) | GCGACCGCGGCCGCTTAGATCA ATCCGTATTGCCG | NotI |
| 15 | TDPE_F_BamHI(Duet) | CGATCGGATCCGATGCAGTACG GTATCTAC | BamHI |
| 16 | TDPE_R_HindIII(Duet) | GCGACCAAGCTTTTACAGAACA GAGGTAGAACC | HindIII |
| 17 | RPI_F_NdeI(Duet) | GCGTTGCATATGAAAATCTCTAT CGGTTCTG | NdeI |

TABLE 6-continued

| SEQ ID NO | Primer Name | Nucleotide Sequence (5'→3') | Restriciton Enzyme |
|---|---|---|---|
| 18 | RPI_R_XhoI(Duet) | GGCAGGCTCGAGTTACAGGTTGATTTTTTCGATG | XhoI |
| 19 | CDPE_F_NcoI(Duet) | CGCAAGCCATGGGCATGAAACACGGTATCTACTAC | NcoI |
| 20 | EDPE_F_NcoI(Duet) | CGCAAGCCATGGGCATGCAGGGTTTTGGCGTC | NcoI |
| 21 | TDPE_F_NcoI(Duet) | CGCAAGCCATGGGCATGCAGTACGGTATCTAC | NcoI |

Then, a recombinant *E. coli* strain was prepared by transforming *E. coli* BL21(DE3) (invitrogen) with the constructed each recombinant vector by the heat shock method (Sambrook and Russell: Molecular Cloning.).

After inoculating the prepared recombinant *E. coli* strain into 5 ml LB-ampicilline medium (Difco), it was shaking cultured at 37° C., 200 rpm until the absorbance (OD) at 600 nm reached 1.5, and after inoculating it into 500 ml LB-ampicilline medium again, it was seed cultured in a shaking incubator of 37° C. Then, when the absorbance at 600 nm of culture solution was 0.5, 1 mM of IPTG (isopropyl-1-thio-β-D-galactopyranoside) was added, to induce overexpression of target enzyme. The culture condition was converted to 16° C. and 150 rpm from the overexpression induction time and maintained for 16 hours.

Example 2. Establishment of Reaction Condition of Allose Producing Strain 2-1. Analysis of Cell Reaction Activity by Temperature To confirm the optimum temperature for producing an allose, reaction was done for 2 hours under 60° C., in 5 mg/ml_DCW range of microbial cell concentration of strain isolated in Example 2, in a 10% (v/v) fructose 1 ml, 50 mM PIPES buffer (pH 7.0) solution, and after finishing (stopping) the reaction by heating to stop the substrate reaction, the temperature showing the maximum activity was measured. Then, the allose conversion rate from a fructose for 2 hours was measured, thereby showing the relative value of allose conversion rate at each temperature (RA (%) that is Y axis value of figure) when the allose conversion rate at the optimum temperature was taken as 100%. The result was shown in the following Table 7 and FIGS. 5 to 7.

Conversion rate (%)=(production/amount of substrate added)*100

Amount of substrate added=residual fructose+ amount of psicose remained+allose production  [Formula]

TABLE 7

| Classification | Conversion rate (%) | | |
|---|---|---|---|
| Temperature (° C.) | RSF_CDPE_RPI (his tag X) | RSF_TDPE_RPI (his tag X) | RSF_EDPE_RPI (his tag X) |
| 40 | 5.46 | 6.39 | 6.84 |
| 45 | 8.50 | 7.27 | 7.32 |
| 50 | 8.51 | 8.12 | 7.81 |
| 55 | 8.17 | 8.57 | 7.28 |
| 60 | 7.90 | 3.99 | 4.94 |
| 70 | 8.04 | 2.68 | 3.71 |

As shown in the Table 7 and FIGS. 5 to 7, it could be confirmed that RSF_TDPE_RPI (FIG. 5) exhibited the optimum activity at 55° C. and RSF_CDPE_RPI (FIG. 6) and RSF_EDPE_RPI (FIG. 7) exhibited the optimum activity at 50° C.

2-2. Analysis of Cell Reaction Activity by pH

To confirm the cell reaction activity by pH, reaction was done for 2 hours at 50° C. under each pH condition using 5 mg/ml_DCW of microbial cell concentration of strain isolated in Example 1 and fructose concentration 10% (v/v) buffer solution, 50 mM sodium citrate (pH 4 to 5), 50 mM sodium phosphate (pH 6 to 8), 50 mM glycine NaOH (pH 9 to 10), respectively, and after finishing (stopping) the reaction by heating to stop the substrate reaction, the pH showing the maximum activity was measured. Then, the allose conversion rate from a fructose for 2 hours was measured, thereby showing the relative value of allose conversion rate at each pH (RA (%) that is Y axis value of figure) when the allose conversion rate at the optimum pH was taken as 100%. The result was shown in the following Table 8 and FIGS. 8 to 10.

Conversion rate (%)=(Production/amount of substrate added)*100

Amount of substrate added=residual fructose+ amount of psicose remained+allose production  [Formula]

TABLE 8

| | | Converstion rate (%) | | |
|---|---|---|---|---|
| Classification | | RSF_CDPE_RPI | RSF_TDPE_RPI | RSF_EDPE_RPI |
| Buffer | pH | (his tag X) | (his tag X) | (his tag X) |
| Sodium citrate | 5 | 0.4 | 0 | 0 |
| | 6 | 6.5 | 8.8 | 8.3 |

TABLE 8-continued

| | | Converstion rate (%) | | |
|---|---|---|---|---|
| Classification | | RSF_CDPE_RPI | RSF_TDPE_RPI | RSF_EDPE_RPI |
| Buffer | pH | (his tag X) | (his tag X) | (his tag X) |
| Sodium | 6 | 4.1 | 5.9 | 6.8 |
| Phosphate | 7 | 6.6 | 10.0 | 9.1 |
| | 8 | 7.4 | 8.9 | 9.6 |
| Glycine- | 9 | 4.4 | 5.2 | 6.5 |
| NaOH | 10 | 2.8 | 1.3 | 2.7 |

As shown in the Table 8 and FIGS. 8 to 10, RSF_TDPE_RPI exhibited the optimum activity at pH 7.0 (FIG. 8), and RSF_CDPE_RPI (FIG. 9) and RSF_EDPE_RPI (FIG. 10) exhibited the optimum activity at pH 8.0.

2-3. Analysis of Metal Ion Requirement of Enzyme

To confirm the metal ion requirement, reaction was done for 2 hours using 1 mM metal ion ($CuCl_2$, $MnCl_2$, $FeSO_4$, $ZnSO_4$, $NiSO_4$, or $CoCl_2$) solution dissolved in 50 mM PIPES buffer solution (pH 7.0 or 8.0, performing at the optimum pH of each enzyme), at 5 mg/ml_DCW of microbial cell concentration of strain isolated in Example 2 and 50° C., respectively, and after finishing (stopping) the reaction by heating for 5 minutes to stop the substrate reaction, the allose production was measured through HPLC analysis by the same method as the Example 3-1. That was treated with no metal ion was used as a control group (Non).

The result was shown in the following Table 9 and FIGS. 11 to 13.

TABLE 9

| | RSF_CDPE_RPI (his tag X) | | RSF_TDPE_RPI (his tag X) | | RSF_EDPE_RPI (his tag X) | |
|---|---|---|---|---|---|---|
| | Conversion rate (%) | RA (%) | Conversion rate (%) | RA (%) | Conversion rate (%) | RA (%) |
| Cu | 0 | 0 | 1.5 | 18 | 1.7 | 18 |
| Mn | 4.7 | 72 | 6.8 | 81 | 8.2 | 90 |
| Ni | 4.3 | 66 | 7.1 | 85 | 7.5 | 83 |
| Fe | 6.5 | 100 | 8.1 | 97 | 9.1 | 100 |
| Co | 4.9 | 76 | 8.3 | 98 | 7.6 | 84 |
| Zn | 0 | 0 | 1.9 | 22 | 1.2 | 14 |
| Non | 5.8 | 90 | 8.4 | 100 | 8.6 | 95 |

As shown in the Table 9 and FIGS. 11 to 13, it was confirmed that in case of CDPE_RPI, the activity was slightly increased by Fe ion (FIG. 11), but all three enzymes did not exhibit the result considerably depending on the metal ion (FIGS. 11 to 13).

In other words, it was confirmed that the activity, conversion rate, thermal stability, etc. were significantly degraded when conventional CDPE, TDPE, EDPE were expressed alone without a metal, but when two enzymes were expressed in one vector at the same time, the conversion reaction was occurred without a metal ion different from conventional each enzyme.

2-4. Analysis of Thermal Stability of Cell Reaction

To confirm the thermal stability of cell reaction, after adding heat to the enzyme at 40 to 50° C. for 24 hours, the strain to which the thermal shock was applied was used for reaction.

Specifically, reaction was done for 2 hours using 50 mM PIPES buffer solution (pH 7.0 or 8.0, performing at the optimum pH of each enzyme), at 5 mg/ml_DCW of microbial cell concentration of strain to which the thermal shock was added and 50° C., respectively, and after finishing (stopping) the reaction by heating for 5 minutes to stop the substrate reaction. The allose conversion rate was measured by the following formula. The result was shown in the following Table 10 (40° C.) and Table 11 (50° C.), and the conversion rate converted into a log value was shown in FIGS. 14 to 16.

Conversion rate (%)=(Production/amount of substrate added)*100

Amount of substrate added=residual fructose+
    amount of psicose remained+allose production     [Formula]

TABLE 10

| | Conversion rate (%) | | |
|---|---|---|---|
| 40° C. Time (h) | RSF_CDPE_RPI (his tag X) | RSF_TDPE_RPI (his tag X) | RSF_EDPE_RPI (his tag X) |
| 0 | 5.4 | 5.4 | 5.7 |
| 2 | 5.8 | 6.4 | 6.0 |
| 4 | 5.2 | 4.4 | 5.7 |
| 6 | 5.3 | 3.9 | 6.2 |
| 20 | 5.5 | 5.5 | 5.6 |

TABLE 11

| | Conversion rate (%) | | |
|---|---|---|---|
| 50° C. Time (h) | RSF_CDPE_RPI (his tag X) | RSF_TDPE_RPI (his tag X) | RSF_EDPE_RPI (his tag X) |
| 0 | 5.4 | 5.4 | 4.7 |
| 2 | 6.1 | 5.0 | 4.0 |
| 4 | 4.4 | 2.8 | 3.5 |
| 6 | 4.0 | 2.3 | 3.0 |
| 8 | 2.0 | 1.0 | 1.5 |
| 20 | 0 | 0 | 0 |

As shown in the Tables 10 to 11 and FIGS. 14 to 16, it was confirmed that the enzyme bore a certain degree of heat for 20 hours or more at 40° C., but when compared to the half-life at each temperature, the activity was decreased by half when heat shock was applied for 3 hours at 50° C.

Example 3. Allose Production 3-1. Allose Production Reaction from 15% (v/v) Fructose To confirm the allose production from a fructose, the allose conversion rate was measured through the following formula by sampling by time as reacting for 0 to 20 hours at 50° C. temperature in 5 mg/ml_DCW range of microbial cell concentration of strais isolated from Example 2, in 15% (v/v) fructose 1 ml as a substrate and 50 mM PIPES buffer solution (pH 7.0 or 8.0, performing at the optimum pH of each enzyme). The result was shown in Table 12 and FIG. 17.

Conversion rate (%)=(Production/amount of substrate added)*100

Amount of substrate added=residual fructose+ amount of psicose remained+allose production    [Formula]

TABLE 12

| Enzyme | Allose conversion rate (%) | Psicose conversion Rate (%) |
|---|---|---|
| RSF_CDPE_RPI (Histag x) | 11.3 | 24.9 |
| RSF_TDPE_RPI (Histag x) | 12.0 | 25.3 |
| RSF_EDPE_RPI (Histag x) | 12.6 | 25.3 |
| RSF_CDPE_RPI (Histag ○) | 13.0 | 24.8 |
| RSF_TDPE_RPI (Histag ○) | 11.5 | 25.3 |
| RSF_EDPE_RPI (Histag ○) | 12.9 | 24.9 |
| ACYC_CDPE_RPI (Histag x) | 11.8 | 25.9 |
| ACYC_TDPE_RPI (Histag x) | 12.8 | 25.7 |
| ACYC_TDPE_RPI (Histag x) | 13.6 | 25.9 |
| ACYC_CDPE_RPI (Histag ○) | 13.4 | 24.7 |
| ACYC_TDPE_RPI (Histag ○) | 13.1 | 25.9 |
| ACYC_EDPE_RPI (Histag ○) | 12.8 | 26.0 |

As shown in the Table 12, as the result of analysis of 12 enzymes reaction conversion, it could be confirmed that the allose was produced from the fructose averagely with approximately 13% of conversion rate, even though there was slight difference between enzymes.

3-2. Allose Production Reaction from 50% (v/v) Fructose

To confirm the allose production from a fructose, the allose conversion rate was measured by sampling by time as reacting for 0 to 20 hours at 50° C. in 5 mg/ml_DCW range of microbial cell concentration of strais isolated from Example 2, in 50% (v/v) fructose 1 ml as a substrate and 50 mM PIPES buffer solution (pH 7.0 or 8.0, performing at the optimum pH of each enzyme). The result was shown in Table 13 and FIG. 18.

TABLE 13

| Enzyme | Allose conversion rate (%) | Psicose conversion rate (%) |
|---|---|---|
| RSF_TDPE_RPI (Histag x) | 10.3 | 25.6 |
| RSF_CDPE_RPI (Histag ○) | 13.1 | 25.1 |
| RSF_EDPE_RPI (Histag ○) | 11.4 | 25.4 |
| ACYC_CDPE_RPI (Histag x) | 13.3 | 26.5 |
| ACYC_TDPE_RPI (Histag x) | 13.0 | 25.3 |
| ACYC_TDPE_RPI (Histag x) | 13.9 | 25.6 |
| ACYC_CDPE_RPI (Histag ○) | 12.7 | 25.6 |
| ACYC_TDPE_RPI (Histag ○) | 11.8 | 26.0 |
| ACYC_EDPE_RPI (Histag ○) | 13.2 | 26.0 |

As can be seen in the Table 13, as the result of analysis of 12 enzymes reaction conversion, it could be confirmed that the allose was produced from the fructose averagely with approximately 13% of conversion rate, even though there was slight difference between enzymes.

Example 4. Preparation of Fusion Enzyme Plasmid and Transformation

The encoding gene of psicose epimerase derived from Ensifer adhaerens was synthesized as a form of polynucleotide modified by optimizing for E. coli (SEQ ID NO: 6) and designated as EDPE. The encoding genes of PRI secured in gDNA of Persephonella marina EX-H1, the polynucleotide optimized for E. coli (SEQ ID NO: 10) were secured as each template through PCR, and they were linked as one template by an overlap PCR method (SEQ ID NO: 22).

A recombinant vector was prepared by inserting the polynucleotide linked as one template into the same restriction site of pET21a which was an expression vector using restriction enzymes NdeI and XhoI. The cleavage map of prepared recombinant vector was described in FIG. 19.

Then, a recombinant strain was prepared by transforming E. coli BL21(DE3) (invitrogen) with the constructed each recombinant vector by the heat shock method (Sambrook and Russell: Molecular Cloning.).

After inoculating the prepared recombinant strain into 5 ml LB-ampicilline medium (Difco), it was shaking cultured at 37° C., 200 rpm until the absorbance (OD) at 600 nm reached 1.5, and after inoculating it into 500 ml LB-ampicilline medium again, it was seed cultured in a shaking incubator of 37° C. Then, when the absorbance at 600 nm of culture solution was 0.5, 1 mM of IPTG (isopropyl-1-thio-β-D-galactopyranoside) was added, to induce overexpression of target enzyme. The culture condition was converted to 16° C. and 150 rpm from the overexpression induction time and maintained for 16 hours. After that, only microbial cells were recovered by centrifugation at 8000 rpm for 20 minutes, and washed twice with 0.85% (w/v) NaCl, and then used for allose production and enzyme purification.

Example 5. Allose Production Reaction Using Fusion Enzyme (Enzyme Reaction)

5-1: Purification of Fusion Enzyme

After suspending the microbial cells recovered in the Example 4 into a lysis buffer (50 mM Tris-HCl, pH 7.0 300 mM NaCl), they were lysated at 4° C. for 20 minutes using a ultrasonic processor (ColepParmer). The lysated solution was centrifuged at 13,000 rpm and 4° C. for 20 minutes to recover the supernatant, and applied for Ni-NTA column equilibrated with a lysis buffer in advance (Ni-NTA Superflow, Qiagen), and then a buffer solution in which 20 mM imidazol and 250 mM imidazol were contained in 50 mM Tris-HCl 300 mM NaCl, pH 7.0 was flowed sequentially. The eluted target protein was converted with a buffer solution for measuring the enzyme activity (50 mM Tris-HCl, pH7.0) and used for the next experiment. The partially purified enzyme could be obtained by the method, and it was confirmed that the size of monomer was about 47 kDa by SDS-PAGE (FIG. 20).

5-2: Allose Production from Fructose

To confirm the allose production from a fructose, the allose conversion rate was measured by sampling by time as reacting for 24 hours at 50° C. in 1.0 mg/ml range of concentration of enzyme purified in Example 6, in 50% (v/v) fructose 1 ml as a substrate and 50 mM PIPES buffer (pH 7.0 or 8.0, performing at the optimum pH of each enzyme). The result was shown in Table 14 and FIG. 21.

TABLE 14

| Hours | EDPE_RPI (%) | CDPE_RPI (%) |
|---|---|---|
| 3 | 7.2 | 7.8 |
| 8 | 11.7 | 11.3 |
| 24 | 13.4 | 13.1 |

As can be seen in the Table 14 and FIG. 20, as the result of analysis of reaction of two enzymes, it was confirmed that the allose was produced with about 13.4% in case of EDPE_RPI_FUSION and with about 13.1% in case of CDPE_RPI_FUSION. In other words, it was confirmed that the expression rate of fusion enzyme was decreased, but the conversion rate reached a similar equilibrium value of 13%, when two enzymes were expressed respectively and reacted.

The invention claimed is:

1. An enzyme for producing an allose from a fructose comprising a fusion protein in which a psicose epimerase and an allose isomerase are connected by a linker peptide, wherein the psicose epimerase comprises an amino acid sequence selected from the group consisting of SEQ ID NOs: 1 to 3, and the allose isomerase comprises the amino acid sequence of SEQ ID NO: 4.

2. The enzyme for producing an allose from a fructose of claim 1, wherein the linker peptide consists of 1 to 6 amino acid sequence.

3. The enzyme for producing an allose from a fructose of claim 1, wherein the fusion protein comprises the amino acid sequence of SEQ ID NO: 23 or 25.

4. The enzyme of claim 1, wherein the enzyme is characterized by producing an allose from a fructose with a conversion rate of 12 to 15%.

* * * * *

SEQUENCE LISTING

<160> NUMBER OF SEQ ID NOS: 25

<210> SEQ ID NO 1
<211> LENGTH: 289
<212> TYPE: PRT
<213> ORGANISM: Artificial Sequence
<220> FEATURE:
<223> OTHER INFORMATION: CDPE

<400> SEQUENCE: 1

Met Lys His Gly Ile Tyr Tyr Ala Tyr Trp Glu Gln Glu Trp Ala Ala
1               5                   10                  15

Asp Tyr Lys Arg Tyr Val Glu Lys Ala Ala Lys Leu Gly Phe Asp Ile
                20                  25                  30

Leu Glu Val Gly Ala Ala Pro Leu Pro Asp Tyr Ser Ala Gln Glu Val
            35                  40                  45

Lys Glu Leu Lys Lys Cys Ala Asp Asp Asn Gly Ile Gln Leu Thr Ala
        50                  55                  60

Gly Tyr Gly Pro Ala Phe Asn His Asn Met Gly Ser Ser Asp Pro Lys
65                  70                  75                  80

Ile Arg Glu Glu Ala Leu Gln Trp Tyr Lys Arg Leu Phe Glu Val Met
                85                  90                  95

Ala Gly Leu Asp Ile His Leu Ile Gly Gly Ala Leu Tyr Ser Tyr Trp
                100                 105                 110

Pro Val Asp Phe Ala Thr Ala Asn Lys Glu Glu Asp Trp Lys His Ser
            115                 120                 125

Val Glu Gly Met Gln Ile Leu Ala Pro Ile Ala Ser Gln Tyr Gly Ile
        130                 135                 140

Asn Leu Gly Met Glu Val Leu Asn Arg Phe Glu Ser His Ile Leu Asn
145                 150                 155                 160

Thr Ser Glu Glu Gly Val Lys Phe Val Thr Glu Val Gly Met Asp Asn
                165                 170                 175

Val Lys Val Met Leu Asp Thr Phe His Met Asn Ile Glu Glu Ser Ser
                180                 185                 190

Ile Gly Asp Ala Ile Arg His Ala Gly Lys Leu Leu Gly His Phe His
            195                 200                 205

Thr Gly Glu Cys Asn Arg Met Val Pro Gly Lys Gly Arg Thr Pro Trp
        210                 215                 220

Arg Glu Ile Gly Asp Ala Leu Arg Glu Ile Glu Tyr Asp Gly Thr Val
225                 230                 235                 240

Val Met Glu Pro Phe Val Arg Met Gly Gly Gln Val Gly Ser Asp Ile
                245                 250                 255

Lys Val Trp Arg Asp Ile Ser Lys Gly Ala Gly Glu Asp Arg Leu Asp
                260                 265                 270

Glu Asp Ala Arg Arg Ala Val Glu Phe Gln Arg Tyr Met Leu Glu Trp
            275                 280                 285

Lys

<210> SEQ ID NO 2
<211> LENGTH: 282
<212> TYPE: PRT
<213> ORGANISM: Artificial Sequence
<220> FEATURE:
<223> OTHER INFORMATION: EDPE

<400> SEQUENCE: 2

Met Gln Gly Phe Gly Val His Thr Ser Met Trp Thr Met Asn Trp Asp

```
1               5                   10                  15
Arg Pro Gly Ala Glu Arg Ala Val Ala Ala Val Lys Tyr Ala Val
                20                  25                  30

Asp Phe Ile Glu Ile Pro Met Leu Asn Pro Pro Ala Val Asp Thr Ala
                35                  40                  45

His Thr Arg Ala Leu Leu Glu Lys Asn Lys Leu Arg Ala Val Cys Ser
    50                  55                  60

Leu Gly Leu Pro Glu Arg Ala Trp Ala Ser Val Arg Pro Asp Ala Ala
65                  70                  75                  80

Ile Glu His Leu Lys Val Ala Ile Asp Lys Thr Ala Asp Leu Gly Gly
                85                  90                  95

Glu Ala Leu Ser Gly Val Ile Tyr Gly Gly Ile Gly Glu Arg Thr Gly
                100                 105                 110

Val Pro Pro Thr Glu Ala Glu Tyr Asp Asn Ile Ala Arg Val Leu Gln
                115                 120                 125

Ala Ala Ala Lys His Ala Lys Thr Arg Gly Ile Glu Leu Gly Val Glu
130                 135                 140

Ala Val Asn Arg Tyr Glu Asn His Leu Ile Asn Thr Gly Trp Gln Ala
145                 150                 155                 160

Val Asp Met Ile Lys Arg Val Gly Ala Asp Asn Val Phe Val His Leu
                165                 170                 175

Asp Thr Tyr His Met Asn Ile Glu Glu Lys Gly Ile Gly Thr Gly Ile
                180                 185                 190

Leu Asp Ala Arg Asp Phe Ile Lys Tyr Ile His Leu Ser Glu Ser Asp
                195                 200                 205

Arg Gly Thr Pro Gly Tyr Gly Asn Cys Ala Trp Asp Glu Ile Phe Ala
                210                 215                 220

Thr Leu Ala Ala Ile Gly Phe Lys Gly Gly Leu Ala Met Glu Ser Phe
225                 230                 235                 240

Ile Asn Met Pro Pro Glu Val Ala Tyr Gly Leu Ala Val Trp Arg Pro
                245                 250                 255

Val Ala Arg Asp Glu Glu Glu Val Met Gly Asn Gly Leu Pro Phe Leu
                260                 265                 270

Arg Asn Lys Ala Arg Gln Tyr Gly Leu Ile
                275                 280

<210> SEQ ID NO 3
<211> LENGTH: 295
<212> TYPE: PRT
<213> ORGANISM: Artificial Sequence
<220> FEATURE:
<223> OTHER INFORMATION: TDPE

<400> SEQUENCE: 3

Met Gln Tyr Gly Ile Tyr Phe Ala Tyr Trp Thr Lys Glu Trp Gln Ala
1               5                   10                  15

Asp Tyr Lys Lys Tyr Ile Asp Lys Val Ser Lys Leu Gly Phe Asp Ile
                20                  25                  30

Leu Glu Ile Ser Cys Ala Ala Leu Lys Asp Gln Tyr Val Ser Asp Ser
            35                  40                  45

Gln Leu Phe Asp Leu Arg Asp Tyr Ala Lys Glu Lys Gly Val Thr Leu
    50                  55                  60

Thr Ala Gly Tyr Gly Pro Ala Lys Gly Glu Asn Leu Ser Ser Ser Asp
65                  70                  75                  80

Asn Arg Val Val Lys Asn Ala Lys Ala Phe Tyr Lys Asp Val Leu Gly
```

85                  90                  95
Lys Leu Asn Lys Leu Asp Ile Arg Leu Leu Gly Gly Gly Leu Tyr Ser
            100                 105                 110

Tyr Trp Pro Val Asp Tyr Ser Leu Pro Ile Asp Lys Ala Gly Asp Trp
        115                 120                 125

Lys Arg Ser Val Glu Asn Ile Arg Glu Ile Ala Ala Ile Ala Ala Asp
    130                 135                 140

Arg Asn Val Val Leu Gly Met Glu Val Leu Asn Arg Phe Glu Gly Tyr
145                 150                 155                 160

Leu Leu Asn Thr Cys Glu Glu Gly Ile Lys Phe Val Asp Glu Val Asn
                165                 170                 175

His Pro Asn Val Lys Val Met Leu Asp Thr Phe His Met Asn Ile Glu
            180                 185                 190

Glu Asp Asn Met Ala Glu Ala Ile Arg Met Ala Gly Asp Lys Leu Gly
        195                 200                 205

His Phe His Ile Gly Glu Gln Asn Arg Lys Val Pro Gly Lys Gly Cys
    210                 215                 220

Ile Pro Trp Asn Ala Ile Gly His Ala Leu Arg Asp Ile Arg Tyr Asn
225                 230                 235                 240

Gly Thr Val Val Met Glu Pro Phe Val Met Pro Gly Gly Thr Ile Gly
                245                 250                 255

Gln Asp Ile Lys Val Trp Arg Asn Leu Leu Pro Glu Thr Ser Glu Thr
            260                 265                 270

Ile Leu Asp Arg Asp Ala Lys Gly Ala Leu Glu Phe Val Lys His Val
        275                 280                 285

Phe Gly Ser Thr Ser Val Leu
    290                 295

<210> SEQ ID NO 4
<211> LENGTH: 148
<212> TYPE: PRT
<213> ORGANISM: Artificial Sequence
<220> FEATURE:
<223> OTHER INFORMATION: RPI

<400> SEQUENCE: 4

Met Lys Ile Ser Ile Gly Ser Asp His Ala Gly Phe Glu Leu Lys Glu
1               5                  10                  15

Ile Ile Lys Asp His Leu Gln Lys Lys Gly Tyr Glu Val Val Asp Lys
            20                  25                  30

Gly Thr Tyr Ser Lys Glu Ser Val Asp Tyr Pro Leu Phe Gly Glu Ala
        35                  40                  45

Val Gly Arg Ser Val Ser Glu Gly Glu Thr Asp Arg Gly Ile Val Ile
    50                  55                  60

Cys Gly Thr Gly Ile Gly Ile Ser Ile Ser Ala Asn Lys Ile Lys Gly
65                  70                  75                  80

Val Arg Ala Ala Leu Cys Thr Asn Glu Tyr Met Ala Arg Met Ser Arg
                85                  90                  95

Lys His Asn Asp Ala Asn Val Leu Ala Leu Gly Ser Arg Val Leu Gly
            100                 105                 110

Ile Asp Leu Ala Leu Ser Ile Val Asp Thr Phe Leu Ser Thr Asp Phe
        115                 120                 125

Glu Gly Gly Arg His Glu Arg Arg Val His Leu Ile Gln Asn Ile Glu
    130                 135                 140

Lys Ile Asn Leu

<210> SEQ ID NO 5
<211> LENGTH: 870
<212> TYPE: DNA
<213> ORGANISM: Artificial Sequence
<220> FEATURE:
<223> OTHER INFORMATION: CDPE(Original)

<400> SEQUENCE: 5

| | |
|---|---|
| atgaagcatg gtatttatta cgcgtactgg aacaggaat gggcagcaga ttacaagcgg | 60 |
| tatgtagaga aggcggcaaa gcttggattc gatatactgg aggttggcgc ggcgccactg | 120 |
| ccggactatt ctgcgcagga ggtaaaggaa ctgaaaaaat gcgccgatga taacggtatc | 180 |
| cagctgaccg cgggatatgg tcccgccttc aatcataata tgggttcctc agatccgaag | 240 |
| atcagggaag aggcgcttca atggtataaa cgcctgttcg aggtgatggc aggccttgat | 300 |
| attcatctga ttggcggagc gctttattca tactggccgg tggactttgc cacagccaat | 360 |
| aaggaagagg actggaagca cagcgtggag ggaatgcaga ttctggcgcc catcgccagc | 420 |
| cagtatggca tcaatctggg aatggaagtc ctgaaccgct tgagagcca tatcttaaat | 480 |
| acttcggaag aaggcgtgaa gttcgtgacg aagtaggca tggataatgt gaaagtcatg | 540 |
| ctggatacgt tccatatgaa catcgaggaa tcgagcattg gcgacgcgat ccgccatgcc | 600 |
| gggaaacttc ttggacactt ccacaccggc gagtgcaacc gcatggtacc cggaaagggc | 660 |
| cgcaccccat ggagggagat cggggatgcc ttgcgcgaga ttgagtatga cggaaccgtg | 720 |
| gttatggagc catttgtacg catgggcgga caggtaggct ctgatatcaa ggtctggaga | 780 |
| gacatcagca agggcgcggg agaggaccgg ctggatgagg atgcaaggcg cgcggtagag | 840 |
| ttccagagat acatgcttga atggaagtaa | 870 |

<210> SEQ ID NO 6
<211> LENGTH: 870
<212> TYPE: DNA
<213> ORGANISM: Artificial Sequence
<220> FEATURE:
<223> OTHER INFORMATION: CDPE(E.coli)

<400> SEQUENCE: 6

| | |
|---|---|
| atgaaacacg gtatctacta cgcgtactgg aacaggaat gggcggcgga ctacaaacgt | 60 |
| tacgttgaaa aagcggcgaa actgggtttc gacatcctgg aagttggtgc ggcgccgctg | 120 |
| ccggactact ctgcgcagga agttaaagaa ctgaaaaaat gcgcggacga caacggtatc | 180 |
| cagctgaccg cgggttacgg tccggcgttc aaccacaaca tgggttcttc tgacccgaaa | 240 |
| atccgtgaag aagcgctgca gtggtacaaa cgtctgttcg aagttatggc gggtctggac | 300 |
| atccacctga tcggtggtgc gctgtactct tactggccgg ttgacttcgc gaccgcgaac | 360 |
| aaagaagaag actggaaaca ctctgttgaa ggtatgcaga tcctggcgcc gatcgcgtct | 420 |
| cagtacggta tcaacctggg tatggaagtt ctgaaccgtt tcgaatctca catcctgaac | 480 |
| acctctgaag aaggtgttaa attcgttacc gaagttggta tggacaacgt taaagttatg | 540 |
| ctggacacct tccacatgaa catcgaagaa tcttctatcg gtgacgcgat ccgtcacgcg | 600 |
| ggtaaactgc tgggtcactt ccacaccggt gaatgcaacc gtatggttcc gggtaaaggt | 660 |
| cgtaccccgt ggcgtgaaat cggtgacgcg ctgcgtgaaa tcgaatacga cggtaccgtt | 720 |
| gttatggaac cgttcgttcg tatgggtggt caggttggtt ctgacatcaa agtttggcgt | 780 |
| gacatctcta aaggtgcggg tgaagaccgt ctggacgaag acgcgcgtcg tgcggttgaa | 840 | ttccagcgtt acatgctgga atggaaatga                                          870

<210> SEQ ID NO 7
<211> LENGTH: 849
<212> TYPE: DNA
<213> ORGANISM: Artificial Sequence
<220> FEATURE:
<223> OTHER INFORMATION: EDPE(Original)

<400> SEQUENCE: 7
atgcagggtt ttggcgtcca tacgagcatg tggaccatga attgggatcg ccccggtgcg         60
gagcgcgccg ttgcggcggc ggtaaaaatac gccgtcgact tcatcgagat cccgatgctc      120
aatccgccgg cggttgatac tgcccatacc agggcgctgc tggagaaaaa caagctgcgc       180
gcggtctgct cgctcggcct gccggagcgc gcctgggcat ccgtccgacc cgatgccgcg       240
atcgagcatc tgaaggtggc gatcgacaag acggccgatc tcggcggcga ggcgctgtcc       300
ggcgtcatct acggcggcat cggcgagcgc accggcgtgc cgccgactga agccgaatac       360
gacaacattg cccgtgtgct gcaggccgcc gccaagcacg ccaaaacccg cggcatcgaa       420
ctgggtgtcg aggcggtcaa ccgctacgag aaccacctga tcaacaccgg ttggcaagcg       480
gtcgacatga tcaagcgggt gggcgccgac aatgtcttcg tgcatctcga tacctaccac       540
atgaacatcg aggaaagggg catcggcacc ggcatcctcg atgcacgcga cttcatcaaa       600
tacatccacc tgtccgaaag cgaccgcggc acgcccggct atggcaattg cgcctgggac       660
gagatcttcg cgacgctggc cgcgatcggt ttcaagggtg gctggcgat ggaaagcttc        720
atcaacatgc cgccggaagt ggcctatggc cttgcggtct ggcggccggt cgccagggac      780
gaagaggaag tgatgggcaa cggcctgccg ttccttagga caaggcccg gcaatacgga       840
ttgatctag                                                               849

<210> SEQ ID NO 8
<211> LENGTH: 887
<212> TYPE: DNA
<213> ORGANISM: Artificial Sequence
<220> FEATURE:
<223> OTHER INFORMATION: TDPE(Original)

<400> SEQUENCE: 8
atgcaatagg tatttatttt gcctattgga caaaggaatg gcaggcggat tacaaaaagt         60
atatcgataa agtatcaaaa ctgggttttg atatactgga gatatcctgt gcagccttga       120
aggatcaata tgtttcggat tcccaacttt ttgatttgcg ggattatgcg aaagagaagg       180
gtgtcaccct gaccgctggc tacggcccgg ctaagggcga aaatcttagt tcttccgata       240
accgggttgt caaaaatgca aaagccttttt ataaggatgt gctgggaaag ctcaacaaac       300
tcgacataag gctgctgggc gggggttat actcatactg gccggttgac tattctctgc        360
ccattgataa ggcgggggac tggaaacggt cagttgaaaa tatcagggaa attgccgcaa      420
tcgccgcaga ccgcaacgtg gtattgggga tggaggtatt aaaccgcttc gaagggtatt      480
tgcttaacac ctgtgaggaa ggaattaagt tgtcgatga agttaatcac ccgaatgtaa       540
aagtcatgct ggatactttt cacatgaata ttgaggaaga taatatggct gaagccatcc      600
gcatggcggg ggataagctt ggcattttc atattggcga acagaaccgc aaggttcccg       660
ggaaaggatg catcccctgg aatgcaattg gtcatgccct gcgggacata cggtacaatg      720
ggacggtggt gatggagccc tttgtcatgc ccgggggaac catagggcag gatataaaag      780

```
<210> SEQ ID NO 9
<211> LENGTH: 912
<212> TYPE: DNA
<213> ORGANISM: Artificial Sequence
<220> FEATURE:
<223> OTHER INFORMATION: TDPE(E.coli)

<400> SEQUENCE: 9
atgcagtacg gtatctactt cgcgtactgg accaaagaat ggcaggcgga ctacaaaaaa      60
tacatcgaca aagtttctaa actgggtttc gacatcctgg aaatctcttg cgcggcgctg     120
aaagaccagt acgtttctga ctctcagctg ttcgacctgc gtgactacgc gaaagaaaaa     180
ggtgttaccc tgaccgcggg ttacggtccg gcgaaaggtg aaaacctgtc ttcttctgac     240
aaccgtgttg ttaaaaacgc gaaagcgttc tacaaagacg ttctgggtaa actgaacaaa     300
ctggacatcc gtctgctggg tggtggtctg tactcttact ggccggttga ctactctctg     360
ccgatcgaca aagcgggtga ctggaaacgt tctgttgaaa acatccgtga atcgcggcg      420
atcgcggcga ccgtaacgt tgttctgggt atggaagttc tgaaccgttt cgaaggttac     480
ctgctgaaca cctgcgaaga aggtatcaaa ttcgttgacg aagttaacca cccgaacgtt     540
aaagttatgc tggacacctt ccacatgaac atcgaagaag acaacatggc ggaagcgatc     600
cgtatggcgg gtgacaaact gggtcacttc cacatcggtg aacagaaccg taaagttccg     660
ggtaaaggtt gcatcccgtg aacgcgatc ggtcacgcgc tgcgtgacat ccgttacaac     720
ggtaccgttg ttatggaacc gttcgttatg ccgggtggta ccatcggtca ggacatcaaa     780
gtttggcgta acctgctgcc ggaaacctct gaaaccatcc tggaccgtga cgcgaaaggt     840
gcgctggaat tcgttaaaca cgttttcggt tctacctctg ttctgctcga gcaccaccac     900
caccaccact ga                                                         912

<210> SEQ ID NO 10
<211> LENGTH: 447
<212> TYPE: DNA
<213> ORGANISM: Artificial Sequence
<220> FEATURE:
<223> OTHER INFORMATION: RPI

<400> SEQUENCE: 10
atgaaaatct ctatcggttc tgaccacgcg ggtttcgaac tgaaagaaat catcaaagac      60
cacctgcaga aaaaaggtta cgaagttgtt gacaaaggta cctactctaa agaatctgtt     120
gactacccgc tgttcggtga agcggttggt cgttctgttt ctgaaggtga aaccgaccgt     180
ggtatcgtta tctgcggtac cggtatcggt atctctatct ctgcgaacaa aatcaaaggt     240
gttcgtgcgg cgctgtgcac caacgaatac atggcgcgta tgtctcgtaa acacaacgac     300
gcgaacgttc tggcgctggg ttctcgtgtt ctgggtatcg acctggcgct gtctatcgtt     360
gacaccttcc tgtctaccga cttcgaaggt ggtcgtcacg aacgtcgtgt tcacctgatc     420
cagaacatcg aaaaaatcaa cctgtaa                                         447

<210> SEQ ID NO 11
<211> LENGTH: 33
<212> TYPE: DNA
<213> ORGANISM: Artificial Sequence
<220> FEATURE:
<223> OTHER INFORMATION: CDPE_F_BamHI(Duet)
```

```
<400> SEQUENCE: 11
cgatcggatc cgatgaaaca cggtatctac tac                                33

<210> SEQ ID NO 12
<211> LENGTH: 31
<212> TYPE: DNA
<213> ORGANISM: Artificial Sequence
<220> FEATURE:
<223> OTHER INFORMATION: CDPE_R_HindIII(Duet)

<400> SEQUENCE: 12
gcgaccaagc ttttatttcc attccagcat g                                  31

<210> SEQ ID NO 13
<211> LENGTH: 30
<212> TYPE: DNA
<213> ORGANISM: Artificial Sequence
<220> FEATURE:
<223> OTHER INFORMATION: EDPE_F_BamHI(Duet)

<400> SEQUENCE: 13
cgatcggatc cgatgcaggg ttttggcgtc                                    30

<210> SEQ ID NO 14
<211> LENGTH: 35
<212> TYPE: DNA
<213> ORGANISM: Artificial Sequence
<220> FEATURE:
<223> OTHER INFORMATION: EDPE_R_NotI(Duet)

<400> SEQUENCE: 14
gcgaccgcgg ccgcttagat caatccgtat tgccg                              35

<210> SEQ ID NO 15
<211> LENGTH: 30
<212> TYPE: DNA
<213> ORGANISM: Artificial Sequence
<220> FEATURE:
<223> OTHER INFORMATION: TDPE_F_BamHI(Duet)

<400> SEQUENCE: 15
cgatcggatc cgatgcagta cggtatctac                                    30

<210> SEQ ID NO 16
<211> LENGTH: 33
<212> TYPE: DNA
<213> ORGANISM: Artificial Sequence
<220> FEATURE:
<223> OTHER INFORMATION: TDPE_R_HindIII(Duet)

<400> SEQUENCE: 16
gcgaccaagc ttttacagaa cagaggtaga acc                                33

<210> SEQ ID NO 17
<211> LENGTH: 31
<212> TYPE: DNA
<213> ORGANISM: Artificial Sequence
<220> FEATURE:
<223> OTHER INFORMATION: RPI_F_NdeI(Duet)

<400> SEQUENCE: 17
gcgttgcata tgaaaatctc tatcggttct g                                  31

<210> SEQ ID NO 18
```

```
<211> LENGTH: 34
<212> TYPE: DNA
<213> ORGANISM: Artificial Sequence
<220> FEATURE:
<223> OTHER INFORMATION: RPI_R_XhoI(Duet)

<400> SEQUENCE: 18
ggcaggctcg agttacaggt tgattttttc gatg                             34

<210> SEQ ID NO 19
<211> LENGTH: 35
<212> TYPE: DNA
<213> ORGANISM: Artificial Sequence
<220> FEATURE:
<223> OTHER INFORMATION: CDPE_F_NcoI(Duet)

<400> SEQUENCE: 19
cgcaagccat gggcatgaaa cacggtatct actac                            35

<210> SEQ ID NO 20
<211> LENGTH: 32
<212> TYPE: DNA
<213> ORGANISM: Artificial Sequence
<220> FEATURE:
<223> OTHER INFORMATION: EDPE_F_NcoI(Duet)

<400> SEQUENCE: 20
cgcaagccat gggcatgcag ggttttggcg tc                               32

<210> SEQ ID NO 21
<211> LENGTH: 32
<212> TYPE: DNA
<213> ORGANISM: Artificial Sequence
<220> FEATURE:
<223> OTHER INFORMATION: TDPE_F_NcoI(Duet)

<400> SEQUENCE: 21
cgcaagccat gggcatgcag tacggtatct ac                               32

<210> SEQ ID NO 22
<211> LENGTH: 1302
<212> TYPE: DNA
<213> ORGANISM: Artificial Sequence
<220> FEATURE:
<223> OTHER INFORMATION: EDPE_RPI_FUSION

<400> SEQUENCE: 22
atgcagggtt ttggcgtcca tacgagcatg tggaccatga attgggatcg ccccggtgcg      60
gagcgcgccg ttgcggcggc ggtaaaatac gccgtcgact tcatcgagat cccgatgctc     120
aatccgccgg cggttgatac tgcccatacc agggcgctgc tggagaaaaa caagctgcgc     180
gcggtctgct cgctcggcct gccggagcgc gcctgggcat ccgtccgacc cgatgccgcg     240
atcgagcatc tgaaggtggc gatcgacaag acgccgatc tcggcggcga ggcgctgtcc      300
ggcgtcatct acggcggcat cggcgagcgc accggcgtgc cgccgactga agccgaatac     360
gacaacattg cccgtgtgct gcaggccgcc gccaagcacg ccaaaacccg cggcatcgaa     420
ctgggtgtcg aggcggtcaa ccgctacgag aaccacctga tcaacaccgg ttggcaagcg     480
gtcgacatga tcaagcgggt gggcgccgac aatgtcttcg tgcatctcga tacctaccac     540
atgaacatcg aggaaaaggg catcggcacc ggcatcctcg atgcacgcga cttcatcaaa     600
tacatccacc tgtccgaaag cgaccgcggc acgcccggct atggcaattg cgcctgggac     660
gagatcttcg cgacgctggc cgcgatcggt ttcaagggtg ggctggcgat ggaaagcttc     720
```

-continued

```
atcaacatgc cgccggaagt ggcctatggc cttgcggtct ggcggccggt cgccagggac     780
gaagaggaag tgatgggcaa cggcctgccg ttccttagga caaggcccg gcaatacgga      840 ttgatctcgg gctctggtat gaaaatctct atcggttctg accacgcggg tttcgaactg     900
aaagaaatca tcaaagacca cctgcagaaa aaaggttacg aagttgttga caaaggtacc     960
tactctaaag aatctgttga ctacccgctg ttcggtgaag cggttggtcg ttctgtttct     1020
gaaggtgaaa ccgaccgtgg tatcgttatc tgcggtaccg gtatcggtat ctctatctct    1080
gcgaacaaaa tcaaaggtgt tcgtgcggcg ctgtgcacca acgaatacat ggcgcgtatg     1140
tctcgtaaac acaacgacgc gaacgttctg gcgctgggtt ctcgtgttct gggtatcgac     1200
ctggcgctgt ctatcgttga caccttcctg tctaccgact cgaaggtgg tcgtcacgaa      1260 cgtcgtgttc acctgatcca gaacatcgaa aaaatcaacc tg                        1302
```

<210> SEQ ID NO 23
<211> LENGTH: 434
<212> TYPE: PRT
<213> ORGANISM: Artificial Sequence
<220> FEATURE:
<223> OTHER INFORMATION: EDPE_RPI_FUSION

<400> SEQUENCE: 23

```
Met Gln Gly Phe Gly Val His Thr Ser Met Trp Thr Met Asn Trp Asp
1               5                   10                  15

Arg Pro Gly Ala Glu Arg Ala Val Ala Ala Val Lys Tyr Ala Val
            20                  25                  30

Asp Phe Ile Glu Ile Pro Met Leu Asn Pro Pro Ala Val Asp Thr Ala
        35                  40                  45

His Thr Arg Ala Leu Leu Glu Lys Asn Lys Leu Arg Ala Val Cys Ser
    50                  55                  60

Leu Gly Leu Pro Glu Arg Ala Trp Ala Ser Val Arg Pro Asp Ala Ala
65                  70                  75                  80

Ile Glu His Leu Lys Val Ala Ile Asp Lys Thr Ala Asp Leu Gly Gly
                85                  90                  95

Glu Ala Leu Ser Gly Val Ile Tyr Gly Gly Ile Gly Glu Arg Thr Gly
            100                 105                 110

Val Pro Pro Thr Glu Ala Glu Tyr Asp Asn Ile Ala Arg Val Leu Gln
        115                 120                 125

Ala Ala Ala Lys His Ala Lys Thr Arg Gly Ile Glu Leu Gly Val Glu
    130                 135                 140

Ala Val Asn Arg Tyr Glu Asn His Leu Ile Asn Thr Gly Trp Gln Ala
145                 150                 155                 160

Val Asp Met Ile Lys Arg Val Gly Ala Asp Asn Val Phe Val His Leu
                165                 170                 175

Asp Thr Tyr His Met Asn Ile Glu Glu Lys Gly Ile Gly Thr Gly Ile
            180                 185                 190

Leu Asp Ala Arg Asp Phe Ile Lys Tyr Ile His Leu Ser Glu Ser Asp
        195                 200                 205

Arg Gly Thr Pro Gly Tyr Gly Asn Cys Ala Trp Asp Glu Ile Phe Ala
    210                 215                 220

Thr Leu Ala Ala Ile Gly Phe Lys Gly Gly Leu Ala Met Glu Ser Phe
225                 230                 235                 240

Ile Asn Met Pro Pro Glu Val Ala Tyr Gly Leu Ala Val Trp Arg Pro
                245                 250                 255
```

```
Val Ala Arg Asp Glu Glu Val Met Gly Asn Gly Leu Pro Phe Leu
            260                 265                 270
Arg Asn Lys Ala Arg Gln Tyr Gly Leu Ile Ser Gly Ser Gly Met Lys
        275                 280                 285
Ile Ser Ile Gly Ser Asp His Ala Gly Phe Glu Leu Lys Glu Ile Ile
    290                 295                 300
Lys Asp His Leu Gln Lys Lys Gly Tyr Glu Val Val Asp Lys Gly Thr
305                 310                 315                 320
Tyr Ser Lys Glu Ser Val Asp Tyr Pro Leu Phe Gly Glu Ala Val Gly
                325                 330                 335
Arg Ser Val Ser Glu Gly Glu Thr Asp Arg Gly Ile Val Ile Cys Gly
            340                 345                 350
Thr Gly Ile Gly Ile Ser Ile Ser Ala Asn Lys Ile Lys Gly Val Arg
        355                 360                 365
Ala Ala Leu Cys Thr Asn Glu Tyr Met Ala Arg Met Ser Arg Lys His
    370                 375                 380
Asn Asp Ala Asn Val Leu Ala Leu Gly Ser Arg Val Leu Gly Ile Asp
385                 390                 395                 400
Leu Ala Leu Ser Ile Val Asp Thr Phe Leu Ser Thr Asp Phe Glu Gly
                405                 410                 415
Gly Arg His Glu Arg Arg Val His Leu Ile Gln Asn Ile Glu Lys Ile
            420                 425                 430
Asn Leu
```

<210> SEQ ID NO 24
<211> LENGTH: 1326
<212> TYPE: DNA
<213> ORGANISM: Artificial Sequence
<220> FEATURE:
<223> OTHER INFORMATION: CDPE_RPI_FUSION

<400> SEQUENCE: 24

```
atgaaacacg tatctactac cgcgtactgg aacaggaat  gggcggcgga ctacaaacgt     60
tacgttgaaa aagcggcgaa actgggtttc gacatcctgg aagttggtgc ggcgccgctg    120
ccggactact ctgcgcagga agttaaagaa ctgaaaaaat cgcgcgacga caacggtatc    180
cagctgaccg cgggttacgg tccggcgttc aaccacaaca tgggttcttc tgacccgaaa    240
atccgtgaag aagcgctgca gtggtacaaa cgtctgttcg aagttatggc gggtctggac    300
atccacctga tcggtggtgc gctgtactct tactggccgg ttgacttcgc gaccgcgaac    360
aaagaagaag actggaaaca ctctgttgaa ggtatgcaga tcctggcgcc gatcgcgtct    420
cagtacggta tcaacctggg tatggaagtt ctgaaccgtt cgaatctca  catcctgaac    480
acctctgaag aaggtgttaa attcgttacc gaagttggta tggacaacgt taaagttatg    540
ctggacacct ccacatgaa  catcgaagaa tcttctatcg gtgacgcgat ccgtcacgcg    600
ggtaaactgc tggtcacttt ccacaccggt gaatgcaacc gtatggttcc gggtaaaggt    660
cgtaccccgt ggcgtgaaat cggtgacgcg ctgcgtgaaa tcgaatacga cggtaccgtt    720
gttatggaac cgttcgttcg tatgggtggt caggttggtt ctgacatcaa agtttggcgt    780
gacatctcta aggtgcgggt gaagaccgt  ctggacgaag acgcgcgtcg tgcggttgaa    840
ttccagcgtt acatgctgga atggaaatcg gctctggta  tgaaaatctc tatcggttct    900
gaccacgcgg gttctgaact gaagaaaatc atcaaagacc acctgcagaa aaaaggttac    960
gaagttgttg acaaaggtac ctactctaaa gaatctgttg actacccgct gttcggtgaa   1020
```

```
gcggttggtc gttctgtttc tgaaggtgaa accgaccgtg gtatcgttat ctgcggtacc    1080
ggtatcggta tctctatctc tgcgaacaaa atcaaaggtg ttcgtgcggc gctgtgcacc    1140
aacgaataca tggcgcgtat gtctcgtaaa cacaacgacg cgaacgttct ggcgctgggt    1200
tctcgtgttc tgggtatcga cctggcgctg tctatcgttg acaccttcct gtctaccgac    1260
ttcgaaggtg gtcgtcacga acgtcgtgtt cacctgatcc agaacatcga aaaaatcaac    1320
ctgtaa                                                                1326
```

<210> SEQ ID NO 25
<211> LENGTH: 441
<212> TYPE: PRT
<213> ORGANISM: Artificial Sequence
<220> FEATURE:
<223> OTHER INFORMATION: CDPE_RPI_FUSION

<400> SEQUENCE: 25

```
Met Lys His Gly Ile Tyr Tyr Ala Tyr Trp Glu Gln Glu Trp Ala Ala
1               5                   10                  15

Asp Tyr Lys Arg Tyr Val Glu Lys Ala Ala Lys Leu Gly Phe Asp Ile
            20                  25                  30

Leu Glu Val Gly Ala Ala Pro Leu Pro Asp Tyr Ser Ala Gln Glu Val
        35                  40                  45

Lys Glu Leu Lys Lys Cys Ala Asp Asp Asn Gly Ile Gln Leu Thr Ala
    50                  55                  60

Gly Tyr Gly Pro Ala Phe Asn His Asn Met Gly Ser Ser Asp Pro Lys
65                  70                  75                  80

Ile Arg Glu Glu Ala Leu Gln Trp Tyr Lys Arg Leu Phe Glu Val Met
                85                  90                  95

Ala Gly Leu Asp Ile His Leu Ile Gly Gly Ala Leu Tyr Ser Tyr Trp
            100                 105                 110

Pro Val Asp Phe Ala Thr Ala Asn Lys Glu Glu Asp Trp Lys His Ser
        115                 120                 125

Val Glu Gly Met Gln Ile Leu Ala Pro Ile Ala Ser Gln Tyr Gly Ile
    130                 135                 140

Asn Leu Gly Met Glu Val Leu Asn Arg Phe Glu Ser His Ile Leu Asn
145                 150                 155                 160

Thr Ser Glu Glu Gly Val Lys Phe Val Thr Glu Val Gly Met Asp Asn
                165                 170                 175

Val Lys Val Met Leu Asp Thr Phe His Met Asn Ile Glu Glu Ser Ser
            180                 185                 190

Ile Gly Asp Ala Ile Arg His Ala Gly Lys Leu Leu Gly His Phe His
        195                 200                 205

Thr Gly Glu Cys Asn Arg Met Val Pro Gly Lys Gly Arg Thr Pro Trp
    210                 215                 220

Arg Glu Ile Gly Asp Ala Leu Arg Glu Ile Glu Tyr Asp Gly Thr Val
225                 230                 235                 240

Val Met Glu Pro Phe Val Arg Met Gly Gly Gln Val Gly Ser Asp Ile
                245                 250                 255

Lys Val Trp Arg Asp Ile Ser Lys Gly Ala Gly Glu Asp Arg Leu Asp
            260                 265                 270

Glu Asp Ala Arg Arg Ala Val Glu Phe Gln Arg Tyr Met Leu Glu Trp
        275                 280                 285

Lys Ser Gly Ser Gly Met Lys Ile Ser Ile Gly Ser Asp His Ala Gly
    290                 295                 300
```

```
Phe Glu Leu Lys Glu Ile Ile Lys Asp His Leu Gln Lys Lys Gly Tyr
305                 310                 315                 320

Glu Val Val Asp Lys Gly Thr Tyr Ser Lys Glu Ser Val Asp Tyr Pro
                325                 330                 335

Leu Phe Gly Glu Ala Val Gly Arg Ser Val Ser Glu Gly Glu Thr Asp
            340                 345                 350

Arg Gly Ile Val Ile Cys Gly Thr Gly Ile Gly Ile Ser Ile Ser Ala
            355                 360                 365

Asn Lys Ile Lys Gly Val Arg Ala Ala Leu Cys Thr Asn Glu Tyr Met
    370                 375                 380

Ala Arg Met Ser Arg Lys His Asn Asp Ala Asn Val Leu Ala Leu Gly
385                 390                 395                 400

Ser Arg Val Leu Gly Ile Asp Leu Ala Leu Ser Ile Val Asp Thr Phe
            405                 410                 415

Leu Ser Thr Asp Phe Glu Gly Gly Arg His Glu Arg Arg Val His Leu
            420                 425                 430

Ile Gln Asn Ile Glu Lys Ile Asn Leu
            435                 440
```